(12) United States Patent
Zeegers

(10) Patent No.: US 10,226,355 B2
(45) Date of Patent: *Mar. 12, 2019

(54) INTERVERTEBRAL DISC PROSTHESIS

(71) Applicant: LDR Medical, Sainte-Savine (FR)

(72) Inventor: Willem Zeegers, Austin, TX (US)

(73) Assignee: LDR Medical, Rosieres Pres Troyes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,937

(22) Filed: Jan. 16, 2018

(65) Prior Publication Data

US 2018/0207000 A1    Jul. 26, 2018

Related U.S. Application Data

(63) Continuation of application No. 15/432,795, filed on Feb. 14, 2017, now Pat. No. 9,867,716, which is a
(Continued)

(30) Foreign Application Priority Data

Dec. 22, 2004 (FR) ..................... 04 13728

(51) Int. Cl.
*A61F 2/44* (2006.01)
*A61B 17/064* (2006.01)
*A61F 2/30* (2006.01)

(52) U.S. Cl.
CPC ........ *A61F 2/4425* (2013.01); *A61B 17/0642* (2013.01); *A61F 2/30721* (2013.01);
(Continued)

(58) Field of Classification Search
CPC .................................................... A61F 2/4425
See application file for complete search history.

(56) References Cited

U.S. PATENT DOCUMENTS

| 566,360 A | 8/1896 | White |
|---|---|---|
| 1,436,573 A | 11/1922 | Joseph et al. |

(Continued)

FOREIGN PATENT DOCUMENTS

| CA | 2472708 A1 | 2/2005 |
|---|---|---|
| CA | 2533473 C | 3/2011 |

(Continued)

OTHER PUBLICATIONS

"U.S. Appl. No. 10/476,565, Amendment After Final filed Nov. 29, 2007", 1 pg.

(Continued)

*Primary Examiner* — Andrew Yang
(74) *Attorney, Agent, or Firm* — Schwegman Lundberg & Woessner, P.A.

(57) ABSTRACT

The present invention relates to an intervertebral disc prosthesis comprising at least three pieces including an upper plate, a lower plate, and a movable core at least in relation to a plate, wherein it also comprises at least one elongated movable osseous anchor comprising an insertion end disposed at a first longitudinal end of the anchor and a retention end disposed at a second longitudinal end of the anchor and a plate-like body disposed between the insertion end and the retention end.

20 Claims, 11 Drawing Sheets

Related U.S. Application Data continuation of application No. 14/726,557, filed on May 31, 2015, now Pat. No. 9,566,164, which is a continuation of application No. 13/603,043, filed on Sep. 4, 2012, now Pat. No. 9,044,339, which is a continuation of application No. 12/360,050, filed on Jan. 26, 2009, now Pat. No. 8,257,439, which is a continuation of application No. 11/109,276, filed on Apr. 18, 2005, now Pat. No. 7,695,516.

(52) U.S. Cl.
CPC ...... *A61F 2/30734* (2013.01); *A61F 2/30749* (2013.01); *A61F 2/442* (2013.01); *A61F 2002/305* (2013.01); *A61F 2002/3038* (2013.01); *A61F 2002/30365* (2013.01); *A61F 2002/30369* (2013.01); *A61F 2002/30387* (2013.01); *A61F 2002/30471* (2013.01); *A61F 2002/30517* (2013.01); *A61F 2002/30576* (2013.01); *A61F 2002/30616* (2013.01); *A61F 2002/30662* (2013.01); *A61F 2002/30729* (2013.01); *A61F 2002/30884* (2013.01); *A61F 2002/443* (2013.01); *A61F 2220/0025* (2013.01); *A61F 2220/0033* (2013.01); *A61F 2220/0091* (2013.01)

(56) References Cited

U.S. PATENT DOCUMENTS

| | | | |
|---|---|---|---|
| 2,836,442 | A | 5/1958 | Moskovitz |
| 3,325,197 | A | 6/1967 | Wehner |
| 3,374,786 | A | 3/1968 | Callender, Jr. |
| 3,486,505 | A | 12/1969 | Morrison |
| 3,791,380 | A | 2/1974 | Dawidowski |
| 3,857,642 | A | 12/1974 | Miller |
| 3,892,232 | A | 7/1975 | Neufeld |
| 3,958,278 | A | 5/1976 | Lee et al. |
| 4,009,712 | A | 3/1977 | Burstein et al. |
| 4,074,542 | A | 2/1978 | Hankosky et al. |
| 4,085,466 | A | 4/1978 | Goodfellow et al. |
| 4,135,506 | A | 1/1979 | Ulrich |
| 4,175,555 | A | 11/1979 | Herbert |
| 4,185,762 | A | 1/1980 | Froehlich |
| 4,237,875 | A | 12/1980 | Termanini |
| 4,309,777 | A | 1/1982 | Patil |
| 4,349,921 | A | 9/1982 | Kuntz |
| 4,379,451 | A | 4/1983 | Getscher |
| 4,409,974 | A | 10/1983 | Freedland et al. |
| 4,432,358 | A | 2/1984 | Fixel |
| 4,488,543 | A | 12/1984 | Tornier |
| 4,494,535 | A | 1/1985 | Haig |
| 4,519,100 | A | 5/1985 | Wills et al. |
| 4,561,432 | A | 12/1985 | Mazor |
| 4,612,920 | A | 9/1986 | Lower |
| 4,621,629 | A | 11/1986 | Koeneman |
| 4,632,101 | A | 12/1986 | Freedland |
| 4,653,489 | A | 3/1987 | Tronzo |
| 4,655,778 | A | 4/1987 | Koeneman |
| 4,657,001 | A | 4/1987 | Fixel |
| 4,664,305 | A | 5/1987 | Blake, III et al. |
| 4,714,469 | A | 12/1987 | Kenna |
| 4,721,103 | A | 1/1988 | Freedland |
| 4,756,711 | A | 7/1988 | Mai et al. |
| 4,759,352 | A | 7/1988 | Lozier |
| 4,759,766 | A | 7/1988 | Buettner-janz et al. |
| 4,759,769 | A | 7/1988 | Hedman et al. |
| 4,787,378 | A | 11/1988 | Sodhi |
| 4,787,908 | A | 11/1988 | Wyss et al. |
| 4,791,918 | A | 12/1988 | Von Hasselbach |
| 4,863,476 | A | 9/1989 | Shepperd |
| 4,874,389 | A | 10/1989 | Downey |
| 4,892,545 | A | 1/1990 | Day et al. |
| 4,898,156 | A | 2/1990 | Gatturna et al. |
| 4,911,718 | A | 3/1990 | Lee et al. |
| 4,932,975 | A | 6/1990 | Main et al. |
| 4,946,378 | A | 8/1990 | Hirayama et al. |
| 4,946,468 | A | 8/1990 | Li |
| 4,955,908 | A | 9/1990 | Frey et al. |
| 4,955,916 | A | 9/1990 | Carignan et al. |
| 4,964,403 | A | 10/1990 | Karas et al. |
| 4,968,315 | A | 11/1990 | Gatturna |
| 4,969,887 | A | 11/1990 | Sodhi |
| 4,973,332 | A | 11/1990 | Kummer |
| 4,973,333 | A | 11/1990 | Treharne |
| 4,997,432 | A | 3/1991 | Keller |
| 5,002,550 | A | 3/1991 | Li |
| 5,002,576 | A | 3/1991 | Fuhrmann et al. |
| 5,007,910 | A | 4/1991 | Anapliotis et al. |
| 5,032,125 | A | 7/1991 | Durham et al. |
| 5,041,114 | A | 8/1991 | Chapman et al. |
| 5,041,116 | A | 8/1991 | Wilson |
| 5,041,139 | A | 8/1991 | Branemark |
| 5,046,513 | A | 9/1991 | Gatturna et al. |
| 5,057,103 | A | 10/1991 | Davis |
| 5,062,851 | A | 11/1991 | Branemark |
| 5,071,437 | A | 12/1991 | Steffee |
| 5,087,266 | A | 2/1992 | Connell et al. |
| 5,098,433 | A | 3/1992 | Freedland |
| 5,116,336 | A | 5/1992 | Frigg |
| 5,122,130 | A | 6/1992 | Keller |
| 5,123,926 | A | 6/1992 | Pisharodi |
| 5,129,901 | A | 7/1992 | Decoste |
| 5,171,281 | A | 12/1992 | Parsons et al. |
| 5,176,681 | A | 1/1993 | Lawes et al. |
| 5,192,303 | A | 3/1993 | Gatturna et al. |
| 5,192,327 | A | 3/1993 | Brantigan |
| 5,197,986 | A | 3/1993 | Mikhail |
| 5,207,679 | A | 5/1993 | Li |
| 5,217,486 | A | 6/1993 | Rice et al. |
| 5,234,447 | A | 8/1993 | Kaster et al. |
| 5,236,460 | A * | 8/1993 | Barber .................. A61F 2/441 403/109.7 |
| 5,242,448 | A | 9/1993 | Pettine et al. |
| 5,246,458 | A | 9/1993 | Graham |
| 5,258,009 | A | 11/1993 | Conners |
| 5,258,031 | A | 11/1993 | Salib et al. |
| 5,290,312 | A | 3/1994 | Kojimoto |
| 5,300,074 | A | 4/1994 | Frigg |
| 5,306,309 | A | 4/1994 | Wagner et al. |
| 5,314,477 | A | 5/1994 | Marnay |
| 5,324,292 | A | 6/1994 | Meyers |
| 5,342,394 | A | 8/1994 | Matsuno et al. |
| 5,356,410 | A | 10/1994 | Pennig |
| 5,356,413 | A | 10/1994 | Martins et al. |
| 5,358,526 | A | 10/1994 | Tornier |
| 5,370,697 | A | 12/1994 | Baumgartner |
| 5,372,599 | A | 12/1994 | Martins |
| 5,397,364 | A | 3/1995 | Kozak et al. |
| 5,401,269 | A | 3/1995 | Buttner-janz et al. |
| 5,417,692 | A | 5/1995 | Goble et al. |
| 5,417,712 | A | 5/1995 | Whittaker et al. |
| 5,425,773 | A | 6/1995 | Boyd et al. |
| 5,429,641 | A | 7/1995 | Gotfried |
| 5,437,674 | A | 8/1995 | Worcel |
| 5,456,721 | A | 10/1995 | Legrand |
| 5,458,601 | A | 10/1995 | Young, Jr. et al. |
| 5,472,452 | A | 12/1995 | Trott |
| 5,478,342 | A | 12/1995 | Kohrs |
| 5,489,210 | A | 2/1996 | Hanosh |
| 5,507,754 | A | 4/1996 | Green et al. |
| 5,507,816 | A | 4/1996 | Bullivant |
| 5,522,845 | A | 6/1996 | Wenstrom, Jr. |
| 5,531,792 | A | 7/1996 | Huene |
| 5,534,004 | A | 7/1996 | Santangelo |
| 5,534,029 | A | 7/1996 | Shima |
| 5,534,030 | A | 7/1996 | Navarro et al. |
| 5,545,229 | A | 8/1996 | Parsons et al. |
| 5,549,617 | A | 8/1996 | Green et al. |
| 5,554,191 | A | 9/1996 | Lahille et al. |
| 5,556,431 | A | 9/1996 | Buttner-janz |
| 5,562,689 | A | 10/1996 | Green et al. |
| 5,562,738 | A | 10/1996 | Boyd et al. |

(56) References Cited

U.S. PATENT DOCUMENTS

| | | |
|---|---|---|
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | Mcdevitt |
| 5,645,596 A | 7/1997 | Kim et al. |
| 5,655,698 A | 8/1997 | Yoon |
| 5,674,294 A | 10/1997 | Bainville et al. |
| 5,676,701 A | 10/1997 | Yuan et al. |
| 5,676,702 A | 10/1997 | Ratron |
| 5,683,465 A | 11/1997 | Shinn et al. |
| 5,702,449 A | 12/1997 | Mckay |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,800,550 A | 9/1998 | Sertich |
| 5,807,403 A | 9/1998 | Beyar et al. |
| 5,824,094 A | 10/1998 | Serhan et al. |
| 5,827,328 A | 12/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,968,098 A | 10/1999 | Winslow |
| 5,980,522 A | 11/1999 | Koros et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A * | 5/2000 | Xavier ................. A61F 2/4425 606/247 |
| 6,080,158 A | 6/2000 | Lin |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,113,637 A | 9/2000 | Gill et al. |
| 6,113,638 A | 9/2000 | Williams et al. |
| 6,129,763 A | 10/2000 | Chauvin et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,241,769 B1 | 6/2001 | Nicholson et al. |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson et al. |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,344,057 B1 | 2/2002 | Rabbe et al. |
| 6,364,880 B1 | 4/2002 | Michelson |
| 6,368,350 B1 | 4/2002 | Erickson et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 * | 9/2002 | Bramlet ................. A61F 2/446 623/17.11 |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,485,517 B1 | 11/2002 | Michelson |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,558,423 B1 | 5/2003 | Michelson |
| 6,558,424 B2 | 5/2003 | Thalgott |
| 6,565,605 B2 | 5/2003 | Goble et al. |
| 6,572,653 B2 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet |
| 6,592,624 B1 | 7/2003 | Fraser et al. |
| 6,599,320 B1 | 7/2003 | Kuslich |
| 6,607,530 B1 | 8/2003 | Carl et al. |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,616,671 B2 | 9/2003 | Landry et al. |
| 6,636,071 B1 | 10/2003 | Yatabe |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'neil |
| 6,652,586 B2 | 11/2003 | Hunter et al. |
| 6,656,224 B2 | 12/2003 | Middleton |
| 6,669,730 B2 | 12/2003 | Ralph et al. |

(56) References Cited

U.S. PATENT DOCUMENTS

| | | | |
|---|---|---|---|
| 6,669,731 | B2 | 12/2003 | Ralph et al. |
| 6,669,732 | B2 | 12/2003 | Serhan et al. |
| 6,673,113 | B2 | 1/2004 | Ralph et al. |
| 6,679,887 | B2 | 1/2004 | Nicholson et al. |
| 6,679,915 | B1 | 1/2004 | Cauthen |
| 6,682,562 | B2 | 1/2004 | Viart et al. |
| 6,695,851 | B2 | 2/2004 | Zdeblick et al. |
| 6,695,882 | B2 | 2/2004 | Bianchi et al. |
| 6,706,068 | B2 | 3/2004 | Ferree |
| 6,709,439 | B2 | 3/2004 | Rogers et al. |
| 6,709,458 | B2 | 3/2004 | Michelson |
| 6,716,247 | B2 | 4/2004 | Michelson |
| 6,719,794 | B2 | 4/2004 | Gerber et al. |
| 6,723,127 | B2 | 4/2004 | Ralph et al. |
| 6,723,128 | B2 | 4/2004 | Uk |
| 6,726,720 | B2 | 4/2004 | Ross et al. |
| 6,730,088 | B2 | 5/2004 | Yeh |
| 6,733,504 | B2 | 5/2004 | Lin et al. |
| 6,733,532 | B1 | 5/2004 | Gauchet et al. |
| 6,733,535 | B2 | 5/2004 | Michelson |
| 6,736,850 | B2 | 5/2004 | Davis |
| 6,740,117 | B2 | 5/2004 | Ralph et al. |
| 6,740,118 | B2 | 5/2004 | Eisermann et al. |
| 6,749,635 | B1 | 6/2004 | Bryan |
| 6,749,636 | B2 | 6/2004 | Michelson |
| 6,752,832 | B2 | 6/2004 | Neumann |
| 6,755,841 | B2 | 6/2004 | Fraser et al. |
| 6,764,512 | B2 | 7/2004 | Keller |
| 6,764,515 | B2 | 7/2004 | Ralph et al. |
| 6,767,367 | B1 | 7/2004 | Michelson |
| 6,770,074 | B2 | 8/2004 | Michelson |
| 6,770,095 | B2 | 8/2004 | Grinberg et al. |
| 6,770,096 | B2 | 8/2004 | Bolger et al. |
| 6,793,678 | B2 | 9/2004 | Hawkins |
| 6,793,679 | B2 | 9/2004 | Michelson |
| 6,800,093 | B2 | 10/2004 | Nicholson et al. |
| 6,805,714 | B2 | 10/2004 | Sutcliffe |
| 6,808,537 | B2 | 10/2004 | Michelson |
| 6,814,737 | B2 | 11/2004 | Cauthen |
| 6,824,565 | B2 | 11/2004 | Muhanna et al. |
| 6,835,206 | B2 | 12/2004 | Jackson |
| 6,849,093 | B2 | 2/2005 | Michelson |
| 6,890,355 | B2 | 5/2005 | Michelson |
| 6,899,735 | B2 | 5/2005 | Coates et al. |
| 6,902,580 | B2 | 6/2005 | Fallin et al. |
| 6,916,340 | B2 | 7/2005 | Metzger et al. |
| 6,923,811 | B1 | 8/2005 | Carl et al. |
| 6,923,830 | B2 | 8/2005 | Michelson |
| 6,936,071 | B1 | 8/2005 | Marnay et al. |
| 6,955,691 | B2 | 10/2005 | Chae et al. |
| 6,962,606 | B2 | 11/2005 | Michelson |
| 6,964,686 | B2 | 11/2005 | Gordon |
| 6,966,929 | B2 | 11/2005 | Mitchell |
| 6,972,019 | B2 | 12/2005 | Michelson |
| 6,972,035 | B2 | 12/2005 | Michelson |
| 6,981,975 | B2 | 1/2006 | Michelson |
| 6,984,245 | B2 | 1/2006 | McGahan et al. |
| 6,986,789 | B2 | 1/2006 | Schultz et al. |
| 6,994,727 | B2 | 2/2006 | Khandkar et al. |
| 7,001,385 | B2 | 2/2006 | Bonutti |
| 7,001,432 | B2 | 2/2006 | Keller et al. |
| 7,008,453 | B1 | 3/2006 | Michelson |
| 7,011,684 | B2 | 3/2006 | Eckman |
| 7,025,787 | B2 | 4/2006 | Bryan et al. |
| 7,033,394 | B2 | 4/2006 | Michelson |
| 7,041,135 | B2 | 5/2006 | Michelson |
| 7,041,136 | B2 | 5/2006 | Goble et al. |
| 7,056,344 | B2 | 6/2006 | Huppert et al. |
| 7,060,097 | B2 | 6/2006 | Fraser et al. |
| 7,060,099 | B2 | 6/2006 | Carli et al. |
| 7,063,701 | B2 | 6/2006 | Michelson |
| 7,063,702 | B2 | 6/2006 | Michelson |
| 7,066,961 | B2 | 6/2006 | Michelson |
| 7,074,237 | B2 | 7/2006 | Goble et al. |
| 7,090,698 | B2 | 8/2006 | Goble et al. |
| 7,094,239 | B1 | 8/2006 | Michelson |
| 7,105,023 | B2 | 9/2006 | Eckman |
| 7,105,024 | B2 | 9/2006 | Richelsoph |
| 7,112,206 | B2 | 9/2006 | Michelson |
| 7,118,579 | B2 | 10/2006 | Michelson |
| 7,118,580 | B1 | 10/2006 | Beyersdorff et al. |
| 7,118,598 | B2 | 10/2006 | Michelson |
| 7,128,760 | B2 | 10/2006 | Michelson |
| 7,128,761 | B2 | 10/2006 | Kuras et al. |
| 7,153,325 | B2 | 12/2006 | Kim et al. |
| 7,163,561 | B2 | 1/2007 | Michelson |
| 7,169,153 | B2 | 1/2007 | Keller |
| 7,175,662 | B2 | 2/2007 | Link et al. |
| 7,179,294 | B2 | 2/2007 | Eisermann et al. |
| 7,198,644 | B2 | 4/2007 | Schultz et al. |
| 7,204,851 | B2 | 4/2007 | Trieu et al. |
| 7,204,852 | B2 | 4/2007 | Marnay et al. |
| 7,211,112 | B2 | 5/2007 | Baynham et al. |
| 7,217,291 | B2 | 5/2007 | Zucherman et al. |
| 7,217,292 | B2 | 5/2007 | Ralph et al. |
| 7,217,293 | B2 | 5/2007 | Branch |
| 7,223,289 | B2 | 5/2007 | Trieu et al. |
| 7,232,463 | B2 | 6/2007 | Falahee |
| 7,232,464 | B2 | 6/2007 | Mathieu |
| 7,291,170 | B2 | 11/2007 | Huppert |
| 7,326,248 | B2 | 2/2008 | Michelson |
| 7,326,250 | B2 | 2/2008 | Beaurain et al. |
| 7,410,501 | B2 | 8/2008 | Michelson |
| 7,419,505 | B2 | 9/2008 | Fleischmann et al. |
| 7,431,735 | B2 | 10/2008 | Liu et al. |
| 7,435,262 | B2 | 10/2008 | Michelson |
| 7,442,209 | B2 | 10/2008 | Michelson |
| 7,445,636 | B2 | 10/2008 | Liu et al. |
| 7,445,635 | B2 | 11/2008 | Fallin et al. |
| 7,455,692 | B2 | 11/2008 | Michelson |
| 7,465,317 | B2 | 12/2008 | Malberg et al. |
| 7,494,508 | B2 | 2/2009 | Zeegers |
| 7,503,933 | B2 | 3/2009 | Michelson |
| 7,540,882 | B2 | 6/2009 | Michelson |
| 7,566,345 | B1 | 7/2009 | Fallin et al. |
| 7,588,590 | B2 | 9/2009 | Chervitz et al. |
| 7,591,851 | B2 | 9/2009 | Winslow et al. |
| 7,594,931 | B2 | 9/2009 | Louis et al. |
| 7,594,932 | B2 | 9/2009 | Aferzon et al. |
| 7,601,170 | B2 | 10/2009 | Winslow et al. |
| 7,608,107 | B2 | 10/2009 | Michelson |
| 7,618,453 | B2 | 11/2009 | Goble et al. |
| 7,618,455 | B2 | 11/2009 | Goble et al. |
| 7,618,456 | B2 | 11/2009 | Mathieu et al. |
| 7,621,955 | B2 | 11/2009 | Goble et al. |
| 7,621,958 | B2 | 11/2009 | Zdeblick et al. |
| 7,632,282 | B2 | 12/2009 | Dinville |
| 7,637,951 | B2 | 12/2009 | Michelson |
| 7,637,954 | B2 | 12/2009 | Michelson |
| 7,641,690 | B2 | 1/2010 | Abdou |
| 7,655,027 | B2 | 2/2010 | Michelson |
| 7,658,766 | B2 | 2/2010 | Melkent et al. |
| 7,682,396 | B2 | 3/2010 | Beaurain et al. |
| 7,695,516 | B2 | 4/2010 | Zeegers |
| 7,695,517 | B2 | 4/2010 | Benzel et al. |
| 7,727,280 | B2 | 6/2010 | McLuen |
| 7,749,252 | B2 | 7/2010 | Zucherman et al. |
| 7,749,274 | B2 | 7/2010 | Razian |
| 7,753,937 | B2 | 7/2010 | Chervitz et al. |
| 7,771,473 | B2 | 8/2010 | Thramann |
| 7,771,475 | B2 | 8/2010 | Michelson |
| 7,776,090 | B2 | 8/2010 | Winslow et al. |
| 7,780,670 | B2 | 8/2010 | Bonutti |
| 7,789,914 | B2 | 9/2010 | Michelson |
| 7,794,502 | B2 | 9/2010 | Michelson |
| 7,799,053 | B2 | 9/2010 | Haid, Jr. et al. |
| 7,799,057 | B2 | 9/2010 | Hudgins et al. |
| 7,799,081 | B2 | 9/2010 | McKinley |
| 7,811,326 | B2 | 10/2010 | Braddock, Jr. et al. |
| 7,819,903 | B2 | 10/2010 | Fraser et al. |
| 7,824,445 | B2 | 11/2010 | Biro et al. |
| 7,833,255 | B2 | 11/2010 | Chow et al. |
| 7,842,088 | B2 | 11/2010 | Rashbaum et al. |
| 7,846,207 | B2 | 12/2010 | Lechmann et al. |

(56) References Cited

U.S. PATENT DOCUMENTS

| | | |
|---|---|---|
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 8,257,439 B2 | 9/2012 | Zeegers |
| 9,044,337 B2 | 6/2015 | Dinville et al. |
| 9,044,339 B2 | 6/2015 | Zeegers |
| 9,566,164 B2 | 2/2017 | Zeegers |
| 9,867,716 B2 | 1/2018 | Zeegers |
| 2001/0020185 A1 | 9/2001 | Ray |
| 2002/0040243 A1 | 4/2002 | Attali et al. |
| 2002/0087212 A1 | 7/2002 | James et al. |
| 2002/0143343 A1 | 10/2002 | Castro |
| 2002/0161444 A1 | 10/2002 | Choi |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0055503 A1 | 3/2003 | O'neil et al. |
| 2003/0069586 A1 | 4/2003 | Errico et al. |
| 2003/0074075 A1 | 4/2003 | James, Jr. et al. |
| 2003/0093153 A1 | 5/2003 | Banick et al. |
| 2003/0093156 A1 | 5/2003 | Metzger et al. |
| 2003/0109928 A1 | 6/2003 | Pasquet et al. |
| 2003/0135279 A1 | 7/2003 | Michelson |
| 2003/0149438 A1 | 8/2003 | Nichols et al. |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0102846 A1 | 5/2004 | Keller et al. |
| 2004/0111160 A1 | 6/2004 | Evans et al. |
| 2004/0117022 A1 | 6/2004 | Marnay et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0210313 A1 | 10/2004 | Michelson |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph et al. |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz et al. |
| 2005/0038512 A1 | 2/2005 | Michelson |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |

(56) References Cited

U.S. PATENT DOCUMENTS

| | | |
|---|---|---|
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | Mcdonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Millard |
| 2006/0058878 A1 | 3/2006 | Michelson |
| 2006/0069437 A1 | 3/2006 | Weber |
| 2006/0069441 A1 | 3/2006 | Zucherman et al. |
| 2006/0085076 A1 | 4/2006 | Krishna et al. |
| 2006/0085077 A1 | 4/2006 | Cook et al. |
| 2006/0095136 A1 | 5/2006 | Mcluen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish, Jr. et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | Mcluen |
| 2006/0259143 A1 | 11/2006 | Navarro et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1 | 4/2007 | Bonutti et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1 | 7/2007 | Rashbaum et al. |
| 2007/0250167 A1 | 10/2007 | Bray et al. |
| 2007/0250168 A1 | 10/2007 | Lechmann et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0145459 A1 | 6/2010 | Mcdonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |

(56) References Cited

U.S. PATENT DOCUMENTS

| | | | |
|---|---|---|---|
| 2011/0082553 A1 | 4/2011 | Abdou | |
| 2011/0087327 A1 | 4/2011 | Lechmann et al. | |
| 2011/0093077 A1 | 4/2011 | Aebi et al. | |
| 2011/0098747 A1 | 4/2011 | Donner et al. | |
| 2011/0118843 A1 | 5/2011 | Mathieu et al. | |
| 2011/0125267 A1 | 5/2011 | Michelson | |
| 2011/0137420 A1 | 6/2011 | Michelson | |
| 2011/0144703 A1 | 6/2011 | Krause et al. | |
| 2011/0160860 A1 | 6/2011 | Johnston et al. | |
| 2011/0166655 A1 | 7/2011 | Michelson | |
| 2011/0166656 A1 | 7/2011 | Thalgott et al. | |
| 2011/0166657 A1 | 7/2011 | Thalgott et al. | |
| 2011/0166658 A1 | 7/2011 | Garber et al. | |
| 2011/0172774 A1 | 7/2011 | Varela | |
| 2011/0196493 A1 | 8/2011 | Pimenta | |
| 2011/0196494 A1 | 8/2011 | Yedlicka et al. | |
| 2011/0202136 A1 | 8/2011 | Brittan et al. | |
| 2011/0208311 A1 | 8/2011 | Janowski | |
| 2011/0208313 A1 | 8/2011 | Michelson | |
| 2011/0230969 A1 | 9/2011 | Biedermann et al. | |
| 2011/0230971 A1 | 9/2011 | Donner et al. | |
| 2011/0295371 A1 | 12/2011 | Moskowitz et al. | |
| 2011/0301713 A1 | 12/2011 | Theofilos | |
| 2011/0301714 A1 | 12/2011 | Theofilos | |
| 2011/0313528 A1 | 12/2011 | Laubert et al. | |
| 2012/0053693 A1 | 3/2012 | Zeegers | |
| 2012/0330424 A1 | 12/2012 | Zeegers | |
| 2015/0257895 A1 | 9/2015 | Zeegers | |
| 2017/0216048 A1 | 8/2017 | Zeegers | |

FOREIGN PATENT DOCUMENTS

| | | |
|---|---|---|
| CN | 101111207 A | 1/2008 |
| CN | 101111207 B | 2/2012 |
| CN | 102551924 A | 7/2012 |
| CN | 102551924 B | 8/2016 |
| DE | 2263842 A1 | 7/1974 |
| DE | 2804936 A1 | 8/1979 |
| DE | 3023353 A1 | 4/1981 |
| DE | 8912648 U1 | 11/1990 |
| DE | 4328690 A1 | 3/1995 |
| DE | 29911422 U1 | 8/1999 |
| DE | 20310432 U1 | 9/2003 |
| DE | 20310433 U1 | 9/2003 |
| DE | 20320454 U1 | 10/2004 |
| DE | 10323363 A1 | 12/2004 |
| DE | 102004027986 A1 | 7/2005 |
| EP | 42271 A1 | 12/1981 |
| EP | 176728 A1 | 4/1986 |
| EP | 0298235 A1 | 1/1989 |
| EP | 0317972 A1 | 5/1989 |
| EP | 0333990 A2 | 9/1989 |
| EP | 0356112 A1 | 2/1990 |
| EP | 0512529 A1 | 11/1992 |
| EP | 0560141 A1 | 9/1993 |
| EP | 0566810 A1 | 10/1993 |
| EP | 0637439 A1 | 2/1995 |
| EP | 0697200 A1 | 2/1996 |
| EP | 0566810 B1 | 8/1996 |
| EP | 0738504 A1 | 10/1996 |
| EP | 0747025 A1 | 12/1996 |
| EP | 0852934 A1 | 7/1998 |
| EP | 0903126 A1 | 3/1999 |
| EP | 0951879 A2 | 10/1999 |
| EP | 0955021 A1 | 11/1999 |
| EP | 0978258 A1 | 2/2000 |
| EP | 1222903 A1 | 7/2002 |
| EP | 1250896 A1 | 10/2002 |
| EP | 1250898 A1 | 10/2002 |
| EP | 1287795 A1 | 3/2003 |
| EP | 1344506 A1 | 9/2003 |
| EP | 1344508 A1 | 9/2003 |
| EP | 1504733 A1 | 2/2005 |
| EP | 1374808 B1 | 12/2005 |
| FR | 2124815 A5 | 9/1972 |
| FR | 2372622 A1 | 6/1978 |
| FR | 2659226 A1 | 9/1991 |
| FR | 2716619 A1 | 9/1995 |
| FR | 2718635 A1 | 10/1995 |
| FR | 2723841 A1 | 3/1996 |
| FR | 2724108 A1 | 3/1996 |
| FR | 2730159 A1 | 8/1996 |
| FR | 2737656 A1 | 2/1997 |
| FR | 2632516 A1 | 12/1999 |
| FR | 2787019 A1 | 6/2000 |
| FR | 2787021 A1 | 6/2000 |
| FR | 2824261 A1 | 11/2002 |
| FR | 2831796 A1 | 5/2003 |
| FR | 2843293 A1 | 2/2004 |
| FR | 2846550 A1 | 5/2004 |
| FR | 2865629 A1 | 8/2005 |
| FR | 2865630 A1 | 8/2005 |
| FR | 2869528 A1 | 11/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2916956 A1 | 12/2008 |
| JP | 2261446 A | 10/1990 |
| WO | WO-9011740 | 10/1990 |
| WO | WO-1991007931 A1 | 6/1991 |
| WO | WO-9113598 A1 | 9/1991 |
| WO | WO-9301771 A1 | 2/1993 |
| WO | WO-9404100 A1 | 3/1994 |
| WO | WO-9515133 A1 | 6/1995 |
| WO | WO-9817209 A2 | 4/1998 |
| WO | WO-9909914 A1 | 3/1999 |
| WO | WO-1999053871 A1 | 10/1999 |
| WO | WO-9956675 A1 | 11/1999 |
| WO | WO-9956676 A1 | 11/1999 |
| WO | WO-1999065412 A1 | 12/1999 |
| WO | WO-1999066864 A1 | 12/1999 |
| WO | WO-0053127 A1 | 9/2000 |
| WO | WO-0074606 A1 | 12/2000 |
| WO | WO-0101893 A1 | 1/2001 |
| WO | WO-0119295 A1 | 3/2001 |
| WO | WO-0143620 A2 | 6/2001 |
| WO | WO-2001041680 A1 | 6/2001 |
| WO | WO-2001062191 A2 | 8/2001 |
| WO | WO-02013732 A2 | 2/2002 |
| WO | WO-02058599 A2 | 8/2002 |
| WO | WO-2002071960 A1 | 9/2002 |
| WO | WO-02089701 A2 | 11/2002 |
| WO | WO-03005939 A2 | 1/2003 |
| WO | WO-2003015646 A2 | 2/2003 |
| WO | WO-03026522 A2 | 4/2003 |
| WO | WO-03039400 A2 | 5/2003 |
| WO | WO-2003045262 A2 | 6/2003 |
| WO | WO-03059212 A1 | 7/2003 |
| WO | WO-03075804 A1 | 9/2003 |
| WO | WO-2003075803 A1 | 9/2003 |
| WO | WO-2004034935 A1 | 4/2004 |
| WO | WO-2004039291 A1 | 5/2004 |
| WO | WO-2004041129 A1 | 5/2004 |
| WO | WO-2004041131 A2 | 5/2004 |
| WO | WO-2004071360 A2 | 8/2004 |
| WO | WO-2004089256 A1 | 10/2004 |
| WO | WO-2005007040 A1 | 1/2005 |
| WO | WO-2005046534 A1 | 5/2005 |
| WO | WO-2005051243 A2 | 6/2005 |
| WO | WO-2005074839 A1 | 8/2005 |
| WO | WO-05104996 A1 | 11/2005 |
| WO | WO-2005117728 A1 | 12/2005 |
| WO | WO-2006016384 A1 | 2/2006 |
| WO | WO-2006047587 A2 | 5/2006 |
| WO | WO-2006062960 A2 | 6/2006 |
| WO | WO-2006120505 A1 | 11/2006 |
| WO | WO-2006130460 A2 | 12/2006 |
| WO | WO-2006136760 | 12/2006 |
| WO | WO-2007000654 A2 | 1/2007 |
| WO | WO-2007034310 A1 | 3/2007 |
| WO | WO-2007063398 A2 | 6/2007 |
| WO | WO-2007078978 A2 | 7/2007 |

(56) References Cited

FOREIGN PATENT DOCUMENTS

| WO | WO-2008099277 A2 | 8/2008 |
|---|---|---|
| WO | WO-2008149223 A2 | 12/2008 |
| WO | WO-2009033100 A1 | 3/2009 |
| WO | WO-2011080535 | 7/2011 |

OTHER PUBLICATIONS

"U.S. Appl. No. 10/476,565, Final Office Action dated May 7, 2007", 8 pgs.
"U.S. Appl. No. 10/476,565, Non Final Office Action dated Jul. 18, 2006", 9 pgs.
"U.S. Appl. No. 10/476,565, Notice of Allowance dated Nov. 29, 2007", 4 pgs.
"U.S. Appl. No. 10/476,565, Response filed Jan. 17, 2007 to Non Final Office Action dated Jul. 18, 2006", 23 pgs.
"U.S. Appl. No. 10/476,565, Response filed Nov. 6, 2007 to Final Office Action dated May 7, 2007", 37 pgs.
"U.S. Appl. No. 10/494,418, Notice of Allowance dated Sep. 20, 2005", 12 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 2008 to Non Final Office Action dated Dec. 26, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/051,710, Final Office Action dated Jul. 20, 2010", 9 pgs.
"U.S. Appl. No. 11/051,710, Final Office Action dated Dec. 15, 2011", 9 pgs.
"U.S. Appl. No. 11/051,710, Non Final Office Action dated Apr. 11, 2011", 9 pgs.
"U.S. Appl. No. 11/051,710, Non Final Office Action dated Oct. 26, 2009", 12 pgs.
"U.S. Appl. No. 11/051,710, Response filed Jan. 20, 2011 to Final Office Action dated Jul. 20, 2010", 19 pgs.
"U.S. Appl. No. 11/051,710, Response filed Apr. 26, 2010 to Non Final Office Action dated Oct. 26, 2009", 19 pgs.
"U.S. Appl. No. 11/051,710, Response filed Oct. 11, 2011 to Non Final Office Action dated Apr. 11, 2011", 19 pgs.
"U.S. Appl. No. 11/098,266, Final Office Action dated Aug. 6, 2007", 8 pgs.
"U.S. Appl. No. 11/098,266, Non Final Office Action dated Mar. 22, 2006", 5 pgs.
"U.S. Appl. No. 11/098,266, Non Final Office Action dated Nov. 29, 2006", 5 pgs.
"U.S. Appl. No. 11/098,266, Notice of Allowance dated Apr. 21, 2008", 7 pgs.
"U.S. Appl. No. 11/098,266, Response filed Feb. 6, 2008 to Final Office Action dated Aug. 6, 2007", 14 pgs.
"U.S. Appl. No. 11/098,266, Response filed May 23, 2007 to Non Final Office Action dated Nov. 29, 2006", 10 pgs.
"U.S. Appl. No. 11/098,266, Response filed Aug. 22, 2006 to Non Final Office Action dated Mar. 22, 2006", 17 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/180,868, Final Office Action dated Nov. 5, 2008", 10 pgs.
"U.S. Appl. No. 11/180,868, Non Final Office Action dated Jan. 22, 2008", 15 pgs.
"U.S. Appl. No. 11/180,868, Response filed May 5, 2009 to Final Office Action dated Nov. 5, 2008", 11 pgs.
"U.S. Appl. No. 11/180,868, Response filed Jul. 21, 2008 to Non Final Office Action dated Jan. 22, 2008", 15 pgs.
"U.S. Appl. No. 11/341,007, Final Office Action dated Dec. 17, 2009", 17 pgs.
"U.S. Appl. No. 11/341,007, Non Final Office Action dated Apr. 13, 2009", 13 pgs.
"U.S. Appl. No. 11/341,007, Notice of Allowance dated Jul. 26, 2010", 6 pgs.
"U.S. Appl. No. 11/341,007, Response filed Jun. 17, 2010 to Final Office Action dated Dec. 17, 2009", 12 pgs.
"U.S. Appl. No. 11/341,007, Response filed Oct. 13, 2009 to Non Final Office Action Apr. 13, 2009", 15 pgs.
"U.S. Appl. No. 11/362,253, Appeal Brief filed Apr. 9, 2012", 38 pgs.
"U.S. Appl. No. 11/362,253, Examiners Answer dated Jun. 20, 2012", 18 pgs.
"U.S. Appl. No. 11/362,253, Final Office Action dated Mar. 8, 2011", 18 pgs.
"U.S. Appl. No. 11/362,253, Final Office Action dated Oct. 15, 2009", 15 pgs.
"U.S. Appl. No. 11/362,253, Non Final Office Action dated Feb. 18, 2009", 14 pgs.
"U.S. Appl. No. 11/362,253, Non Final Office Action dated Jun. 18, 2010", 17 pgs.
"U.S. Appl. No. 11/362,253, Response filed Apr. 15, 2010 to Final Office Action dated Oct. 15, 2009", 24 pgs.
"U.S. Appl. No. 11/362,253, Response filed Aug. 18, 2009 to Non Final Office Action dated Feb. 18, 2009", 15 pgs.
"U.S. Appl. No. 11/362,253, Response filed Aug. 18, 2009 to Office Action dated Feb. 18, 2009", 15 pgs.
"U.S. Appl. No. 11/362,253, Response filed Dec. 20, 2010 to Non Final Office Action dated Jun. 18, 2010", 18 pgs.
"U.S. Appl. No. 11/676,237, Appeal Brief filed Oct. 17, 2011", 41 pgs.
"U.S. Appl. No. 11/676,237, Final Office Action dated Sep. 15, 2010", 12 pgs.
"U.S. Appl. No. 11/676,237, Non Final Office Action dated Feb. 16, 2012", 13 pgs.
"U.S. Appl. No. 11/676,237, Non Final Office Action dated Mar. 20, 2009", 10 pgs.
"U.S. Appl. No. 11/676,237, Non Final Office Action dated Dec. 18, 2009", 11 pgs.
"U.S. Appl. No. 11/676,237, Response filed Jun. 18, 2010 to Non Final Office Action dated Dec. 18, 2009", 15 pgs.
"U.S. Appl. No. 11/676,237, Response filed Sep. 21, 2009 to Non Final Office Action dated Mar. 20, 2009", 13 pgs.
"U.S. Appl. No. 12/025,677, Non Final Office Action dated Oct. 7, 2011", 9 pgs.
"U.S. Appl. No. 12/025,677, Response filed Apr. 9, 2012 to Non Final Office Action dated Oct. 7, 2011", 16 pgs.
"U.S. Appl. No. 12/134,884, Non Final Office Action dated Jan. 31, 2012", 7 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.

(56) References Cited

OTHER PUBLICATIONS

"U.S. Appl. No. 12/360,050, Notice of Allowance dated Mar. 26, 2012", 5 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/391,086, Non Final Office Action dated Jul. 29, 2010", 10 pgs.
"U.S. Appl. No. 12/391,086, Notice of Allowance dated Apr. 15, 2011", 6 pgs.
"U.S. Appl. No. 12/391,086, Response filed Jan. 31, 2011 to Non Final Office Action dated Jul. 29, 2010", 16 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Nov. 18, 2011 to Non Final Office Action dated May 18, 2011", 13 pgs.
"U.S. Appl. No. 12/435,955, Non Final Office Action dated Oct. 11, 2011", 8 pgs.
"U.S. Appl. No. 12/435,955, Response filed Apr. 11, 2012 to Non Final Office Action dated Oct. 11, 2011", 12 pgs.
"U.S. Appl. No. 12/527,373, Non Final Office Action dated Dec. 21, 2011", 7 pgs.
"U.S. Appl. No. 12/955,898, Non Final Office Action dated Jun. 1, 2012", 27 pgs.
"U.S. Appl. No. 12/955,898, Response filed Apr. 19, 2012 to Restriction Requirement dated Mar. 19, 2012", 11 pgs.
"U.S. Appl. No. 12/955,898, Restriction Requirement dated Mar. 19, 2012", 9 pgs.
"U.S. Appl. No. 13/603,043, Final Office Action dated Jul. 24, 2014", 11 pgs.
"U.S. Appl. No. 13/603,043, Non Final Office Action dated Apr. 9, 2013", 13 pgs.
"U.S. Appl. No. 13/603,043, Non Final Office Action dated Nov. 21, 2013", 11 pgs.
"U.S. Appl. No. 13/603,043, Notice of Allowance dated Feb. 10, 2015", 5 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/603,043, Response filed Dec. 24, 2014 to Final Office Action dated Jul. 24, 2014", 11 pgs.
"U.S. Appl. No. 14/726,557, Final Office Action dated Jun. 17, 2016", 8 pgs.
"U.S. Appl. No. 14/726,557, Non Final Office Action dated Dec. 30, 2015", 12 pgs.
"U.S. Appl. No. 14/726,557, Notice of Allowance dated Oct. 3, 2016", 6 pgs.
"U.S. Appl. No. 14/726,557, Response filed May 2, 2016 to Non Final Office Action dated Dec. 30, 2015", 33 pgs.
"U.S. Appl. No. 14/726,557, Response filed Sep. 19, 2016 to Final Office Action dated Jun. 17, 2016", 10 pgs.
"U.S. Appl. No. 15/432,795, Notice of Allowance dated Sep. 8, 2017", 8 pgs.
"U.S. Appl. No. 15/432,795, Preliminary Amendment filed Feb. 14, 2017", 5 pgs.
"France Application Serial No. 0213833, Preliminary Search Report dated Jul. 10, 2003", 2 pgs.
"France Application Serial No. 2730159, Preliminary Search Report dated Sep. 29, 1995", 1 pg.
"France Application Serial No. 2824261, Preliminary Search Report dated Feb. 25, 2002", 4 pgs.
"France Application Serial No. 2831796, Preliminary Search Report dated Aug. 2, 2002", 2 pgs.
"France Application Serial No. 2865629, Preliminary Search Report dated Sep. 14, 2004", 2 pgs.
"France Application Serial No. 2865630, Preliminary Search Report dated Jan. 12, 2005", 2 pgs.
"France Application Serial No. 2869528, Preliminary Search Report dated Dec. 13, 2004", 3 pgs.
"France Application Serial No. 2879436, Preliminary Search Report dated Aug. 11, 2005", 2 pgs.
"France Application Serial No. 2887762, Preliminary Search Report dated Dec. 21, 2005", 2 pgs.
"France Application Serial No. 2891135, Preliminary Search Report dated Jun. 27, 2006", 2 pgs.
"France Application Serial No. 2893838, Preliminary Search Report dated Aug. 4, 2006", 2 pgs.
"France Application Serial No. 2916956, Preliminary Search Report dated Jan. 30, 2008", 3 pgs.
"France Application Serial No. 9404832, Preliminary Search Report dated Jan. 16, 1995", 1 pg.
"International Application Serial No. PCT/IB2002/002998, International Preliminary Examination Report dated Dec. 22, 2003", 8 pgs.
"International Application Serial No. PCT/IB2002/002998, International Search Report dated Sep. 16, 2003", 6 pgs.
"International Application Serial No. PCT/IB2002/004642, International Preliminary Examination Report dated Apr. 1, 2004", 4 pgs.
"International Application Serial No. PCT/IB2002/004642, International Search Report dated Jul. 2, 2003", 2 pgs.
"International Application Serial No. PCT/IB2003/004872, International Preliminary Examination Report dated Mar. 1, 2005", 6 pgs.
"International Application Serial No. PCT/IB2003/004872, International Search Report dated Mar. 3, 2004", 3 pgs.
"International Application Serial No. PCT/IB2005/000280, International Preliminary Report on Patentability dated Jan. 16, 2006", 8 pgs.
"International Application Serial No. PCT/IB2005/000280, International Search Report dated Jun. 24, 2005", 5 pgs.
"International Application Serial No. PCT/IB2005/000280, Written Opinion dated Jun. 24, 2005", 8 pgs.
"International Application Serial No. PCT/IB2005/001151, International Preliminary Report on Patentability dated Jun. 28, 2006", 5 pgs.
"International Application Serial No. PCT/IB2005/001151, International Search Report dated Sep. 12, 2005", 3 pgs.
"International Application Serial No. PCT/IB2005/001151, Written Opinion dated Sep. 12, 2005", 5 pgs.
"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2006/001781, International Preliminary Report on Patentability dated Jul. 19, 2007", 6 pgs.
"International Application Serial No. PCT/IB2006/001781, International Search Report dated Mar. 22, 2007", 3 pgs.
"International Application Serial No. PCT/IB2006/001781, Written Opinion dated Mar. 22, 2007", 6 pgs.

(56) References Cited

OTHER PUBLICATIONS

"International Application Serial No. PCT/IB2006/002632, International Preliminary Report on Patentability dated Aug. 14, 2007", 5 pgs.

"International Application Serial No. PCT/IB2006/002632, International Search Report dated Feb. 23, 2007", 3 pgs.

"International Application Serial No. PCT/IB2006/002632, Written Opinion dated Feb. 23, 2007", 5 pgs.

"International Application Serial No. PCT/IB2006/003418, International Preliminary Report on Patentability dated Nov. 12, 2007", 8 pgs.

"International Application Serial No. PCT/IB2006/003418, International Search Report dated Jul. 24, 2007", 6 pgs.

"International Application Serial No. PCT/IB2006/003418, Written Opinion dated Jul. 24, 2007", 8 pgs.

"International Application Serial No. PCT/IB2008/000349, International Preliminary Report on Patentability dated May 29, 2009", 10 pgs.

"International Application Serial No. PCT/IB2008/000349, International Search Report dated Jan. 12, 2009", 7 pgs.

"International Application Serial No. PCT/IB2008/000349, Written Opinion dated Jan. 12, 2009", 10 pgs.

"International Application Serial No. PCT/IB2008/001484, International Preliminary Report on Patentability dated Aug. 5, 2009", 6 pgs.

"International Application Serial No. PCT/IB2008/001484, International Search Report dated Feb. 16, 2009", 5 pgs.

"International Application Serial No. PCT/IB2008/001484, Written Opinion dated Feb. 16, 2009", 8 pgs.

"International Application Serial No. PCT/IB2009/008048, International Search Report dated Feb. 2, 2011", 6 pgs.

"Mobidisc (Website)", [Online] Retrieved from the internet: <www.ldrmedical.fr/mobidisc.htm>, (Sep. 19, 2004), 1 pg.

"USPTO OA of Feb. 18, 2009 in U.S. Appl. No. 11/632,253", 14 pgs.

Bouduk, N, et al., "A biological basis for instantaneous centres of rotation of the vertebral column", Proc institution Mechanical Engineers, (Jun. 16, 1995), 177-183.

Gertzban, S D, et al., "Centrode Patterns and Segmental Instability in Degenerative Disc Disease", BSc, M. Tile, MD, BSc, {Med}, FRCS ©, and B. Cruickshank, MD, FRCPath, Spine, vol. 10, No. 3 (Jan. 21, 1984), 257-261.

Griffith, S L, et al., "A Multicenter Retrospective Study of the Clinical Results of the LINK SB Charite Intervertebral Prosthesis", vol. 19, No. 16, (Mar. 21, 1994), 1842-1849.

Haher, T R, et al., "Instantaneous Axis of Rotation as a Function of the Three Columns of the Spine", MS, Spine, vol. 17, No. 6, (Jan. 9, 1992), S149-S154.

Haher, T R, et al., "The Effect of the Three Columns of the Spine on the Instantaneous Axis of Rotation in Flexion and Extension", Spine, vol. 16, No. 8, (Apr. 16, 1991), S312-S318.

Klein, J A, et al., "Relocation of the Bending Axis During Flexion-Extension of Lumbar Intervertebral Discs and its Implications for Prolapse", Spine, vol. 8, No. 6, (Nov. 18, 1982), 659-664.

Kostuik, J P, "Alternatives to Spinal Fusion", vol. 29, No. 4, (Oct. 4, 1998), 701-715.

Liu, X, et al., "A New Technique for the Three-Dimensional Study of the Spine in Vitro and in Vivo by Using a Motion-Analysis System", Journal of Spinal Disorders, vol. 10, No. 4, (Jan. 30, 1997), 329-338.

Pearcy, M J, et al., "Instantaneous Axis of Rotation of the Lumbar Intervertebral Joints", vol. 13, No. 9, (Nov. 15, 1987), 1033-1041.

Seligman, S D, "Computer Analysis of Spinal Segment Motion in Degenerative Disc Disease With and Without Axial Loading", Spine, vol. 9., No. 6, (Dec. 31, 1983), 566-573.

White III, A A, et al., "Clinical Biomechanics of the Spine", 2nd Edition, J.B. Lippincott Co., (1990), 128-130.

Yoshioka, T, et al., "Motion Characteristics of the Normal Lumbar Spine in Young Adults: Instantaneous of Axis of Rotation and Vertebral Center Motion Analysis", Journal of Spinal Disorders, vol. 3, No. 2, (1990), 103-113.

\* cited by examiner

INTERVERTEBRAL DISC PROSTHESIS

CROSS-REFERENCE TO RELATED APPLICATIONS

The present application is a continuation of copending U.S. patent application Ser. No. 15/432,795 filed Feb. 14, 2017, and issuing as U.S. Pat. No. 9,867,716 on Jan. 16, 2018, which is a continuation U.S. application Ser. No. 14/726,557 filed May 31, 2015, and issuing as U.S. Pat. No. 9,566,164 on Feb. 14, 2017, which is a continuation of copending U.S. application Ser. No. 13/603,043 filed Sep. 4, 2012, and issuing as U.S. Pat. No. 9,044,339 on Jun. 2, 2015, which is a continuation of U.S. application Ser. No. 12/360,050 filed Jan. 26, 2009, and issuing as U.S. Pat. No. 8,257,439 on Sep. 4, 2012, which is a continuation of U.S. application Ser. No. 11/109,276, filed Apr. 18, 2005, and issuing as U.S. Pat. No. 7,695,516 on Apr. 13, 2010, which claims priority to French Patent Application No. 0413728, filed in FRANCE on Dec. 22, 2004, respectively, and the contents of all of these prior applications are incorporated herein by reference in their entirety.

BACKGROUND

The present invention relates to an intervertebral disc prosthesis, intended to be substituted for fibro-cartilaginous discs ensuring a bond between the vertebrae of the spinal column.

Various types of intervertebral disc prostheses are known in the prior art. Numerous prostheses, such as for example in the patent application WO 02 089 701 and WO 2004/041129, are constituted in a lower plate and an upper plate forming a sort of cage around a central core. A part of these prostheses enables the upper plate to swivel in relation to the central core and optionally permits the central core to slide in relation to the lower plate. This sliding of the central core in relation to the lower plate allows spontaneous positioning of the core in the ideal position to absorb constraints imposed on the prosthesis, during movements made by the patient wearing the prosthesis. The displacement of the core, co-operating with at least a plate about an uneven surface, enables an inclination between the plates of the prosthesis which facilitates the mobility of the patient wearing the prosthesis. The displacement of the core also prevents it from creeping under load, when subjected to major constraints. A part of these prostheses have osseous anchorage means allowing to attach these prostheses to the vertebrae between which they are intended to be inserted.

However, the size of the vertebrae varies greatly from person to person, for a same vertebra in a given position in the spinal column, but also for a given person depending on the position of the vertebrae in the spinal column between which a prosthesis is intended to be inserted. The intervertebral disc prostheses must be of a suitable size for the vertebrae between which they are intended to be inserted, depending on the person and on the position of these vertebrae in the spinal column. Moreover, depending on the spinal column disorder of the patient wearing the prosthesis, it is sometimes preferable that the prosthesis allows a correction of this disorder. The prostheses can thus be used to correct an inclination defect of the vertebrae, such as, for example, lordosis. To have prostheses that are suitable for as large a majority of cases as possible, many different prostheses with different plate sizes and inclinations must therefore be envisaged. This multiplicity of prostheses has the major inconvenience of high manufacturing costs and high stock levels. In this context, it is beneficial to provide a prosthesis that may be adapted to different sizes of vertebrae while allowing for different inclinations of the plates. Such a prosthesis would reduce stock levels and manufacturing costs.

One object of the present invention is to provide an intervertebral disc prosthesis allowing limited movements of the different pieces of the prosthesis between one another and comprising a core used to restrict its displacement in at least one direction.

This aim is achieved by an intervertebral disc prosthesis comprising at least three pieces including an upper plate, a lower plate, and a movable core at least in relation to a plate, having two anatomic adaptation elements each of which has, on one hand, a surface in contact with a surface of a vertebra and, on the other hand, a surface of which at least a part of has a surface in contact with at least a part of the plate opposite to which the anatomic adaptation element is mounted, the anatomic adaptation elements being fixed onto the plates via fixation means.

In other embodiments, the anatomic adaptation elements include crowns which surround the plates and prolong respectively their upper and lower surfaces to present contact surfaces of the prosthesis with the adjacent vertebrae are larger. In other embodiments, the crowns of the anatomic adaptation elements of various sizes are adapted on the plates in order to adapt them to vertebrae of different sizes.

According to another feature of some embodiments, the anatomic adaptation elements are anatomic plates, which cover the plates and prolong respectively their upper and lower surfaces to present contact surfaces of the prosthesis with the adjacent vertebrae which are bigger than when there are no anatomic adaptation elements, the anatomic plates being of various sizes in various embodiments to adapt the plates to vertebrae of different sizes.

According to another feature of some embodiments, the anatomic adaptation elements act to effectively and symmetrically prolong the upper and lower surfaces respectively of the upper and lower plates to present an equivalent prolongation of these surfaces on the different anterior, posterior and lateral edges of the plates.

According to another feature of some embodiments, the anatomic adaptation elements act to effectively and asymmetrically prolong the upper and lower surfaces respectively of the upper and lower plates to present a bigger prolongation of these surfaces on at least one of the anterior, posterior and lateral edges of the plates than on the other edges.

According to another feature of some embodiments, the upper surface of the core is in contact with at least one part of the lower surface of the upper plate and the lower surface of the core is in contact with at least one part of the upper surface of the lower plate.

According to another feature of some embodiments, at least one part of the surface of at least a plate is concave and complementary with a convex surface of the core with which it is in contact.

According to another feature of some embodiments, at least one part of the surface of at least a plate is plane and complementary with a plane surface of the core with which it is in contact.

According to another feature of some embodiments, male and female cooperation means situated in the vicinity of the edges of at least one plate and the core limit preferably, without excessive friction, the movements in translation of the core relative to the selected plate, according to an axis substantially parallel to selected plate, and limit or suppress the rotational movement of the core relative to the selected plate, about an axis substantially perpendicular to the selected plate.

According to another feature of some embodiments, the dimensions of each male cooperation means are slightly less than those of each female cooperation means so as to allow clearance between the core and the plate in embodiments equipped with these cooperation means.

According to another feature of some embodiments, the dimensions of each male cooperation means are substantially the same as those of each female cooperation means so as to prevent any clearance between the core and the plate equipped with these cooperation means.

According to another feature of some embodiments, the cooperation means of the plate are female cooperation means co-operating with male cooperation means of the core.

According to another feature of some embodiments, the male cooperation means of the core are two blocks situated on the two side edges of the core and the female cooperation means of the plate are four walls situated, in pairs, on each of the two side edges of this plate.

According to another feature of some embodiments, the fixation means of the anatomic adaptation elements on the plates of the prosthesis are reversible and allow changing the anatomic adaptation elements fixed in a movable manner onto the plates of the prosthesis.

According to another feature of some embodiments, the fixation means of the anatomic adaptation elements on the plates consist in fixation means present on the anatomic adaptation elements and complementary with fixation means present on the plates of the prosthesis.

According to another feature of some embodiments, the anatomic adaptation elements are fixed onto the plates via, on one hand, contact with at least a part of their surfaces which face at least a part of the plates and, on the other hand, contact of their fixation means with the complementary fixation means present on the plates of the prosthesis.

According to another feature of some embodiments, the fixation means of the anatomic adaptation elements on the plates consist in male fixation means present on the anatomic adaptation elements and that cooperate with the female fixation means present on the plates of the prosthesis or inversely.

According to another feature of some embodiments, the female fixation means present on the plates of the prosthesis consist of plane surfaces present on the edges of the plates of the prosthesis.

According to another feature of some embodiments, the female fixation means present on the plates of the prosthesis consist of recesses made in the edges of the other plate of the prosthesis.

According to another feature of some embodiments, the female fixation means present on the plates of the prosthesis consist of recesses made in the edges of the female cooperation means of the plates of the prosthesis.

According to another feature of some embodiments, the female fixation means present on the plates of the prosthesis consist of plane surfaces present on the edges of one of the plates and in recesses made in the female cooperation means of the edges of the other plate of the prosthesis.

According to another feature of some embodiments, the female fixation means present on at least one of the plates of the prosthesis consist of plane surfaces present on at least a first edge of one of the plates and in recesses made in at least a second edge of the plate of the prosthesis, the second edge geometrically facing a first edge of the plate.

According to another feature of some embodiments, at least one of the female fixation means present on the plates of the prosthesis comprises at least a notch allowing blocking the male fixation means of the anatomic adaptation elements on the selected female fixation means.

According to another feature of some embodiments, the fixation means of the anatomic adaptation elements on the plates consist of female fixation means present on the anatomic adaptation elements and co-operating with male intermediary means which can also cooperate with the female fixation means present on the plates of the prosthesis.

According to another feature of some embodiments, the anatomic adaptation elements are fixed onto the plates via, on one hand, contact of at least a part of their upper and lower surface with at least a part of respectively the upper and lower plates and, on the other hand, contact of the male intermediary means with the female fixation means present on the anatomic adaptation elements and with the female fixation means present on the plates of the prosthesis.

According to another feature of some embodiments, the male intermediary means possess securing means fixing the male intermediary means in a position to cooperate with both the female fixation means of the anatomic adaptation elements and the female fixation means present on the plates of the prosthesis.

According to another feature of some embodiments, the male intermediary means consist of a sliding plate in the female fixation means present on the anatomic adaptation elements to cooperate with the female fixation means present on the plates of the prosthesis, the securing means of the male intermediary means consisting of at least an irregularity present on at least one side of the selected plate that cooperates with an opening in the female fixation means of the anatomic adaptation elements and/or in the female fixation means of the plates, thus fixing the male intermediary means in a position where they cooperate with both the female fixation means of the anatomic adaptation elements and the female fixation means present on the plates of the prosthesis.

According to another feature of some embodiments, the securing means of the male intermediary means consist of a bore in the male intermediary means and in the female fixation means present on the anatomic adaptation elements, the bore in the female fixation means of the anatomic adaptation elements capable of receiving a securing pin fixing the male intermediary means in the position to cooperate with the female fixation means present on the plates of the prosthesis.

According to another feature of some embodiments, the median planes representing the upper and lower surfaces of each of the anatomic adaptation elements are substantially parallel or form an acute angle, the inclination obtained by such an angle allowing adaptation of the overall shape of the prosthesis to the anatomy of the spinal column and in some embodiments ameliorate inclination defects of the vertebrae of the patient for whom the prosthesis is intended.

According to another feature of some embodiments, the same anatomic adaptation elements may be assembled with different plates whose upper and lower surfaces create different angles.

According to another feature of some embodiments, an angle between the upper surface of the upper plate and the lower surface of the lower plate is imposed by creation of angles between the upper and lower surfaces of the lower plate and/or the upper plate, or by restricting, with the cooperation means, movements of the core about a position imposing an inclination of at least one of the plates.

According to another feature of some embodiments, the same plates are assembled with cores of different thicknesses and/or sizes and/or shapes.

According to another feature of some embodiments, the anatomic adaptation elements comprise movable osseous anchorage elements that are fixed onto the anatomic adaptation elements upon fixing the anatomic adaptation elements onto the plates, inserting the prosthesis between the vertebrae or adjusting the relative position of the different elements of the prosthesis.

According to another feature of some embodiments, the movable osseous anchorage elements of the anatomic adaptation elements consist of at least a plate equipped with notches oriented to resist the removal of the plate once it has been inserted into a vertebra, a far end of the plate bearing a part curved to fold over itself that may interlock as a hook onto an edge of an opening made in the vicinity of the periphery of the anatomic adaptation elements.

According to another feature of some embodiments, the part, curved to fold over itself, of the notched plate of the movable osseous anchorage means of the anatomic adaptation elements in prolonged with a second plate also equipped with notches oriented to resist removal once it has been inserted into the vertebra.

According to another feature of some embodiments, the anatomic adaptation elements comprise movable osseous anchorage elements consisting of at least one winglet that may be inserted in a groove formed in the adjacent surfaces of the vertebrae between which the prosthesis is to be implanted, said winglet comprising notches oriented to resist ejection of the prosthesis outside its housing between the vertebrae, a far end of the winglet bearing a part curved to fold over itself that may be interlocked as a hook onto an edge of an opening made in the vicinity of the periphery of the anatomic adaptation elements.

According to another feature of some embodiments, the winglet further comprises a pin having dimensions adapted to fit preferably tightly, into a groove of the anatomic adaptation elements and/or the plates.

BRIEF DESCRIPTION OF THE FIGURES

Other features and advantages of the invention will emerge more clearly from the description herein below, given in reference to the attached diagrams, in which.

DETAILED DESCRIPTIONS

Figure 1:
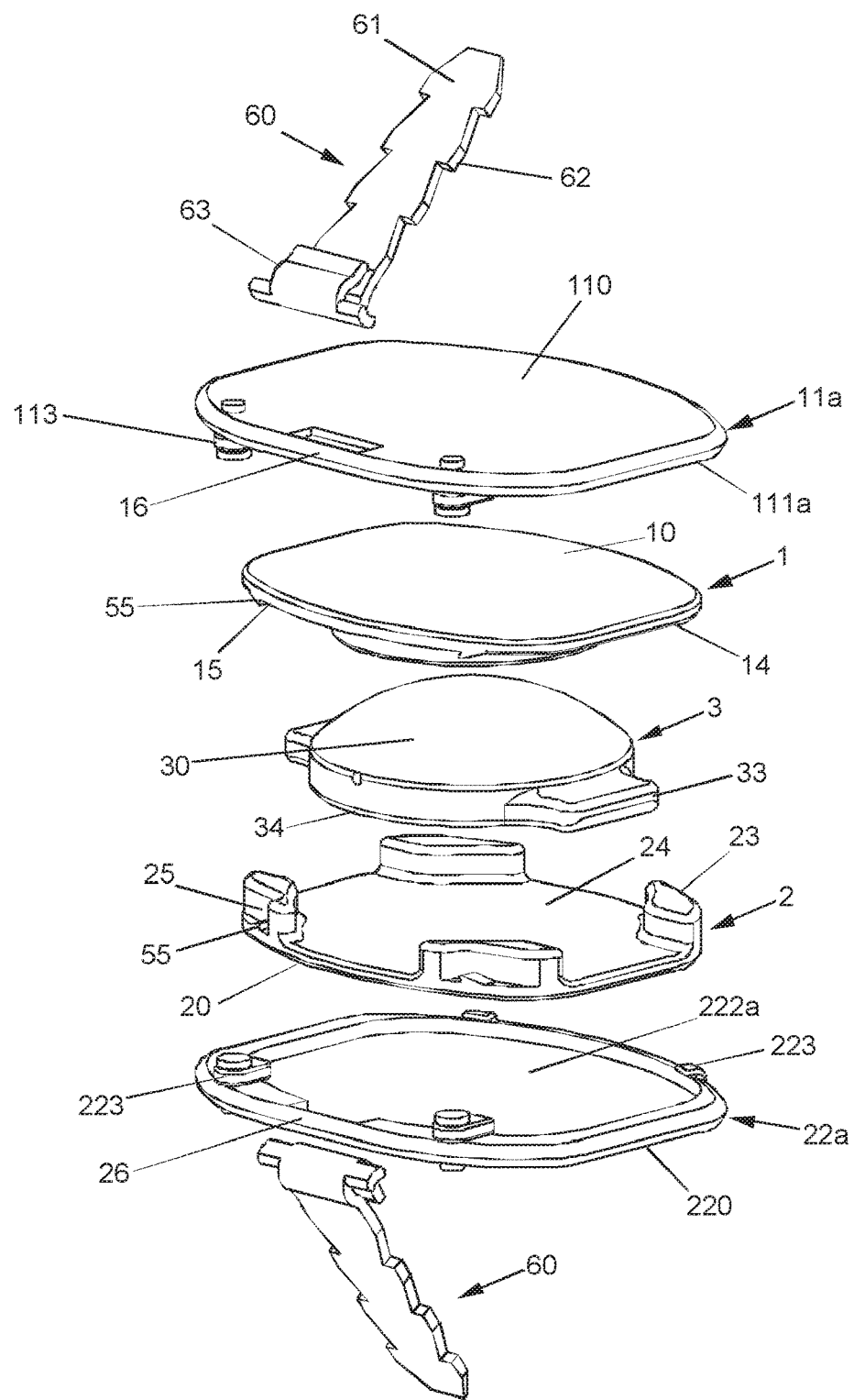
FIG. 1 illustrates an exploded perspective view of the different elements of the prosthesis according to an embodiment of the invention.

The intervertebral disc prosthesis according to the present invention has an upper plate (1) articulated in relation to a lower plate (2) by means of a core (3). Each of the plates (1, 2) is equipped with an anatomic adaptation element (11, 22) allowing adjustment of the overall size of the prosthesis to the size of the vertebrae. Thus the variable size adaptability reduces the cost of manufacturing prostheses and their varieties. One advantage of the prosthesis according to the invention is that it comprises simple parts whose anatomic adaptation elements (11, 22) can be sized so as to adapt to different vertebrae of the spinal column. For example, the thickness of the prosthesis may be adjusted to the intervertebral gap and/or the inclination of the plates (1, 2) of the prosthesis may be adapted to the inclination of the vertebrae of the patient. Even though the anatomic adaptation elements (11, 22) allow adjustment of the prosthesis to different sizes of vertebrae, plates (1, 2) and core (3) of differing sizes and shapes can be used where desired.

Anatomic adaptation elements (11, 22) of the prosthesis (for example, plates 11a and 22a or crowns 11b or 22b) include an upper element (11) and a lower element (22). Upper element (11) has, an upper surface (110) of which at least a part presents a surface in contact with a lower surface of a first vertebra and, a lower surface (111a) or lower edge (111b) at least a part of which presents a surface in contact with a part of upper plate (1). Lower element (22) has a lower surface (220), at least a part of which presents a surface in contact with an upper surface of a second vertebra and has, an upper surface (222a) or upper edge (222b) at least a part of which presents a surface in contact with a part of the lower plate (2). Each of the two anatomic adaptation elements (11, 22) is fixed onto the plates (1, 2) via respective fixation means (113, 223).

The core (3) of various embodiments varies in thickness from approximately 3 to 15 mm, depending on the vertebrae between which the prosthesis is to be inserted. Core (3) may in some embodiments, for example, be made of polyethylene, a compressible material simulating the physical properties of elasticity of natural intervertebral discs.

In some embodiments of the invention, core (3) has a convex part on at least a part of at least one of its upper (30) and lower (34) surfaces. In the embodiments illustrated in FIGS. 1 to 9, it is the upper surface (30) of the core (3) which is convex and complementary with a concave part (140) of the lower surface (14) of the upper plate (1), whereas the lower surface (34) of the core (3) is plane and complementary with at least a plane part of the upper surface (24) of the lower plate (2). The concave part (140) of the lower surface (14) of the upper plate (1), as particularly visible in FIGS. 4A, 4B, 5A, 5B and 5C, has a circular periphery. In other possible embodiments (not shown), a part of the lower surface (34) of the core (3) may be convex and complementary with a concave part of the upper surface (24) of the lower plate (2), whereas the upper surface (30) of the core (3) is plane and complementary with at least a plane part of the lower surface (14) of the upper plate (1). In other embodiments (not shown), the concave surface lies on a part of one of the upper (30) and lower (34) surfaces of the core (3) and cooperates with a convex surface which lies on a part of a surface of one of the plates (1, 2). In some different embodiments (not shown), the non convex or non concave surface of the core (3) can respectively be concave or convex, to a slight degree.

In the embodiments illustrated in FIGS. 1 to 9, the concave part (140) of the lower surface (14) of the upper plate (1) complementary with the convex part of the upper surface (34) of the core (3) allows inclination of the upper plate (1) when the patient wearing the prosthesis bends over. The cooperation between the concave surface (140) and the convex surface (34) presents a surface of articulation with the prosthesis, due to this inclination of the upper plate (1) in relation to the core (3). The center of this articulation is typically at the tip of the convex surface (34) of the core (3). In the illustrated embodiments, the lower surface of the core (3) and the upper surface of the lower plate (2) are plane so as to permit clearance of the core (3) in relation to the lower plate (2), both in translation according to an axis substantially parallel to the lower plate (2), and in rotation about an axis substantially perpendicular to the lower plate (2). During movement by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) in relation to the lower plate (2) thus allow the patient to move, and, optionally, to eliminate the defects of positioning the prosthesis. This clearance likewise has the advantage of preventing premature wear due to the constraints applied to the prosthesis.

The core (3) also has male or female cooperation means (33) complementary with respectively female or male cooperation means (23) present on at least one of the plates (1, 2). These male and female cooperation means (23, 33) situated in the vicinity of the edges of at least one plate (1, 2) and of the core (3) limit, preferably without excessive friction, movements in translation of the core (3) in relation to this plate (1, 2), according to an axis substantially parallel to this plate (1, 2), and limit or suppress the movements in rotation of the core (3) in relation to this plate (1, 2), about an axis substantially perpendicular to this plate (1, 2). The dimensions of each male cooperation means (33) may be slightly less than those of each female cooperation means (23) so as to allow slight clearance between the core (3) and the plate (1, 2) equipped with these cooperation means. The dimensions of each male cooperation means (33) may also be substantially the same as those of each female cooperation means (23) so as to prevent any clearance between the core (3) and the plate (1, 2) equipped with these cooperation means.

Figure 2:
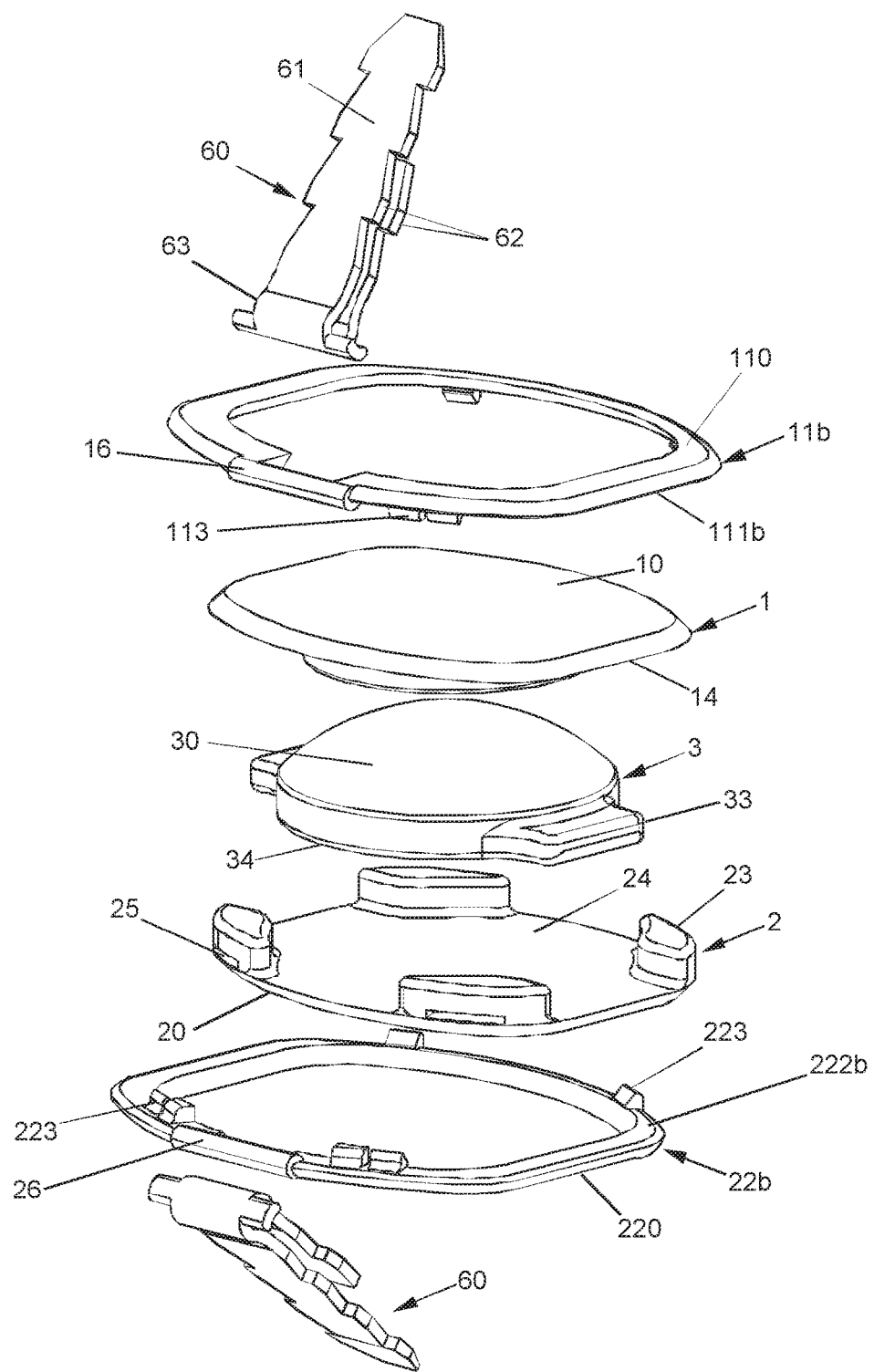
FIG. 2 illustrates an exploded perspective view of the different elements of the prosthesis according to another embodiment of the invention.
Figure 3:
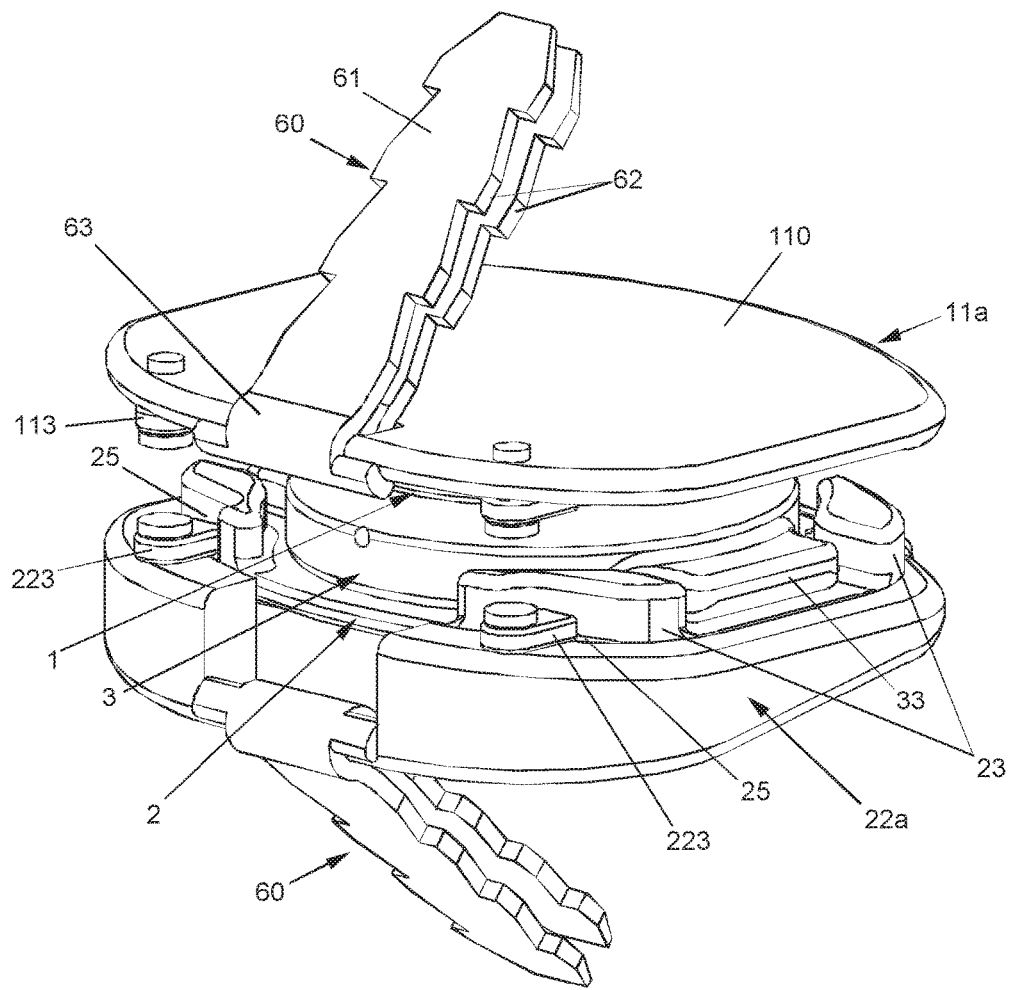
FIG. 3 illustrates a perspective view of the prosthesis according to another embodiment of the invention.

In the embodiment in FIGS. 1 to 3, the core (3) has male cooperation means (33) complementary with female cooperation means (23) present on the lower plate (2). The male cooperation means (33) of the core (3) are, for example, hasps or blocks substantially parallelepiped in shape, present on the side edges of the core (3), as particularly visible in FIGS. 1 to 3. The female cooperation means (23) can consist, for example, of four walls situated, in pairs, on each of the two side edges of the lower plate (2). These walls may, in some cases, be curved to the centre of the prosthesis, so as to cover at least a part of the male cooperation means (33) of the core (3) and avoid lifting the core (3) and the upper plate (1). These cooperation means (23, 33) also prevent the core (3) from ejecting out of the prosthesis, in the event of too much constraint on the prosthesis. In an alternative embodiment, the dimensions of each male cooperation means (33) of the core (3) may be substantially the same as those of each female cooperation means (23) of the lower plate (2), so as to avoid any clearance of the core (3) in relation to the lower plate (2), both in translation and/or in rotation. In the latter case, the only permitted movement of the prosthesis is the inclining of the upper plate (1) in relation to the core (3). In an alternative embodiment, the core (3) has female cooperation means, consisting, for example, of complementary recesses of the male means present on the lower plate (2). These male means of the lower plate (2) may consist, for example, of two blocks or two nibs, curved for example to the interior of the prosthesis and facing one another on two edges of the lower plate (2). The nibs can, for example, be replaced by a block with a bore on which is fixed a hasp by way of a pin penetrating the bore. In another alternative embodiment, the lower plate (2) has half dog points. The core (3), by way of complement, has wells under its lower surface. The dimensions of the half dog points of the lower plate (2) and of the wells of the core (3) will be adapted, by choice, by a slight clearance of the core (3) in translation and in rotation or by no clearance, according to the desired result. In other alternatives, the cooperation means may be located on the core (3) and on the upper plate (1), instead of the lower plate (2). These are just some examples of such means as those of skill will appreciate after understanding this disclosure.

The description of a preferred embodiment will now be considered in reference to FIG. 1. In this embodiment, upper and lower anatomic adaptation elements consist of anatomic plates (11a, 22a), which respectively cover the upper (1) and lower (2) plates. The upper (222a) and lower (111a) surfaces of lower (22a) and upper (11a) anatomic adaptation plates may be reinforced in which respectively the lower (2) and upper (1) plates are housed. In another alternative, these upper (222a) and lower (111a) surfaces of the anatomic adaptation elements can be plane and comprise stoppers which, as for the aforementioned reinforcement, prevent the lower (2) and upper (1) plates respectively from moving in relation to the anatomic adaptation elements. The upper (222a) and lower (111a) surfaces of lower (22a) and upper (11a) anatomic adaptation elements respectively prolong the upper (10) and lower (20) surfaces of the upper (1) and lower (2) plates, to present contact surfaces of the prosthesis with the adjacent vertebrae which are larger than instances in which there are no anatomic adaptation elements (11a, 22a). Different sizes of the anatomic plates of the anatomic adaptation elements (11a, 22a) can be adapted to a single unit created by the two plates (1, 2) and the core (3), to provide contact between the prosthesis and the vertebrae of differing sizes.

In the embodiment of the prosthesis according to the invention illustrated in FIG. 2, anatomic adaptation elements (11b, 22b) consist of crowns which surround upper (1) and lower (2) plates. In this embodiment, the edges of upper (10) and lower (20) surfaces of upper (1) and lower (2) plates are bevelled and complementary with respect to the lower (111b) and upper (222b) inside edges of upper (11b) and lower (22b) crowns, respectively. This inclined shape of the edges of plates (1, 2) and of anatomic adaptation crowns (11b, 22b) cooperates with fixation means (113, 223) of the anatomic adaptation elements to maintain anatomic adaptation crowns (11b, 22b) fixed in the plane of upper (1) and lower (2) plates of the prosthesis, respectively. The anatomic adaptation crowns (11b, 22b) prolong upper (10) and lower (20) surfaces of upper (1) and lower (2) plates, to present contact surfaces of the prosthesis with the adjacent vertebrae which are larger than when there are no anatomic adaptation elements (11, 22). In the same manner as for the aforementioned anatomic plates (11a, 22a), a single unit created by the two plates (1, 2) and the core (3) can thus be adjusted to vertebrae of differing sizes, due to different sizes of crowns (11b, 22b) of the anatomic adaptation elements (11, 22).

In many preferred embodiments, the anatomic adaptation elements (11, 22) may symmetrically or asymmetrically prolong upper (10) and lower (20) surfaces, respectively of upper (1) and lower (2) plates. Thus, for example, the anterior edge of the anatomic adaptation elements (11, 22) may have a larger contact surface with the vertebrae than its posterior edge, so that the center of articulation of the prosthesis (described above) is centered in relation to the natural axis of the spinal column, that meaning off center to the rear of the vertebrae of a ⅔-⅓ section.

Many preferred embodiments, are helpful in the correction of the defects of lordosis. The presence of an angle between the upper and lower surfaces of the prosthesis, in contact with the adjacent vertebrae, is often desirable. Such an angle may be obtained with an upper plate (1), whose median planes representing its lower (14) and upper (10) surfaces create an angle. In other embodiments, lower plate (2) exhibits median planes representing lower (20) and upper (24) surfaces which create an angle. In other embodiments at least one of the anatomic adaptation elements (11, 22) has median planes of the respective structures lower and upper surfaces which create an angle that may be represented by thus, a single unit having two plates (1, 2) and core (3) may be used, for example, to induce or not lordosis, depending on which anatomic adaptation elements (11, 22) are associated with it. In the embodiment illustrated in FIG. 3, lower surface (220) of lower anatomic plate (22a) creates an angle with upper surface (222a). Such an angle which a slightly offset position of the core (3) in relation to the centre of the prosthesis may also be implemented. This slightly offset position of the core (3) may, for example, be maintained with an adjustable positioning of the male and female cooperation means (23, 33). If the surgeon wishes, for example, to induce lordosis within a range of values, a prosthesis may be selected whose core (3) can have slight clearance in translation and in rotation relative to lower plate (2), but about a position imposing a slight permanent inclination of at least one of the plates, due to an accurate adjustment of the cooperation means (23, 33) between core (3) and lower plate (2). Thus, in several preferred embodiments, the median planes representing upper (110, 222a) and lower (111a, 220) surfaces of the anatomic adaptation elements (11, 22) may be substantially parallel or form an acute angle. The inclination obtained by such an angle allows adaptation of the overall shape of the prosthesis to the anatomy of the spinal column or to reduce or correct inclination defects of the vertebrae of the patient for whom the prosthesis is intended. The same anatomic adaptation elements (11, 22) can be assembled with different plates (1, 2) whose upper (10, 24) and lower (14, 20) surfaces create different angles. In other instances, plates (1, 2), whose upper (10, 24) and lower (14, 20) surfaces are parallel, are assembled with anatomic adaptation elements (11, 22) having upper (110, 222a) and lower (111a, 220) surfaces which exhibit different angles. This angle between upper (10) surface of upper plate (1) and lower surface (20) of lower plate (2) may be imposed either by the fact that the median planes representing the lower (20, 14) and upper (24, 10) surfaces of the lower plate (2) and/or the upper plate (1) create an angle, or by restricting, thanks to the cooperation means (23, 33), movements of the core (3) about a position imposing an inclination of at least one of the plates (1, 2).

Illustrated in FIGS. 1 to 3 are movable osseous anchorage means (60) of anatomic adaptation elements (11, 22). Osseous anchorage means (60) may be fixed onto the anatomic adaptation elements (11, 22) upon fixing them onto the plates (1, 2) and/or upon inserting the prosthesis between vertebrae. Thus, the surgeon may easily position the prosthesis between the vertebrae and then insert the osseous anchorage means (60) once the prosthesis has been correctly positioned. In the embodiment presented in FIG. 1, these movable osseous anchorage means (60) consist of a plate (61) equipped with notches (62) oriented to resist removal of plate (61) once it has been inserted into the vertebra. Plate (61) can, of course, be replaced by a rod in the shape of a nail, for example, with or without notches (62) to resist against its removal from the vertebra. A far end of plate (61) bears a part (63) curved to fold over itself. This curved part forms a kind of a hook intended to be interlocked onto an edge (16, 26) of an opening made in the vicinity of the periphery of the anatomic adaptation elements (11, 22). This edge (16, 26) of the opening creates a sort of rod onto which the osseous anchorage means (60) interlock. The curved part (63) allows clasping the osseous anchorage means (60) onto the rod-like edge (16, 26) of anatomic adaptation elements (11, 22). This rod-like edge may be replaced by any equivalent means that attach to the osseous anchorage means (60). In the embodiments illustrated in FIGS. 1 to 9, rod-like edge (16, 26) is located an anterior edge of anatomic adaptation elements (11, 22). This allows the surgeon access after insertion via anterior means (through accessing the vertebrae from their anterior face). If the implanting of the prosthesis is to be done via posterior means, anatomic adaptation elements (11, 22) may have rod-like edge (16, 26) located on the posterior edge. If the implanting of the prosthesis is to be done via lateral means, anatomic adaptation elements (11, 22) may have a rod-like edge (16, 26) located on at least one of their edges. In the embodiment illustrated in FIGS. 2 and 3, hooked part (63), curved to fold over itself, of the notched plate (61) of movable osseous anchorage means (60) of anatomic adaptation crowns (11b, 22b) prolong with a second plate (61) which may be equipped with notches (62) oriented to resist against removal of plate (61) once inserted. In the embodiment illustrated in FIG. 2, second plate (61) is shorter than first plate and in the embodiment illustrated in FIG. 3, it is as long as the first plate. Where osseous anchorage means (60) locks onto the rod-like edge (16, 26) allows it to have a variable angle which facilitates the attaching of the prosthesis. Depending on its encumbrance, the surgeon will have a choice of angles according to which he wishes to drive the osseous anchorage means (60) into the vertebrae. Moreover, because osseous anchorage means (60) may be inserted after positioning the prosthesis between the vertebrae there can be adjustment of the relative position of the different elements (1, 2, 3) of the prosthesis. Inserting the prosthesis generates constraints on the elements of the prosthesis which are movable in relation to each other. Thus, there is a misalignment. The surgeon may, with embodiments hereof, adjust the position of the prosthesis between the vertebrae and adjust the relative position of the elements of the prosthesis between themselves prior to definitively attaching the prosthesis.

Figure 10A:
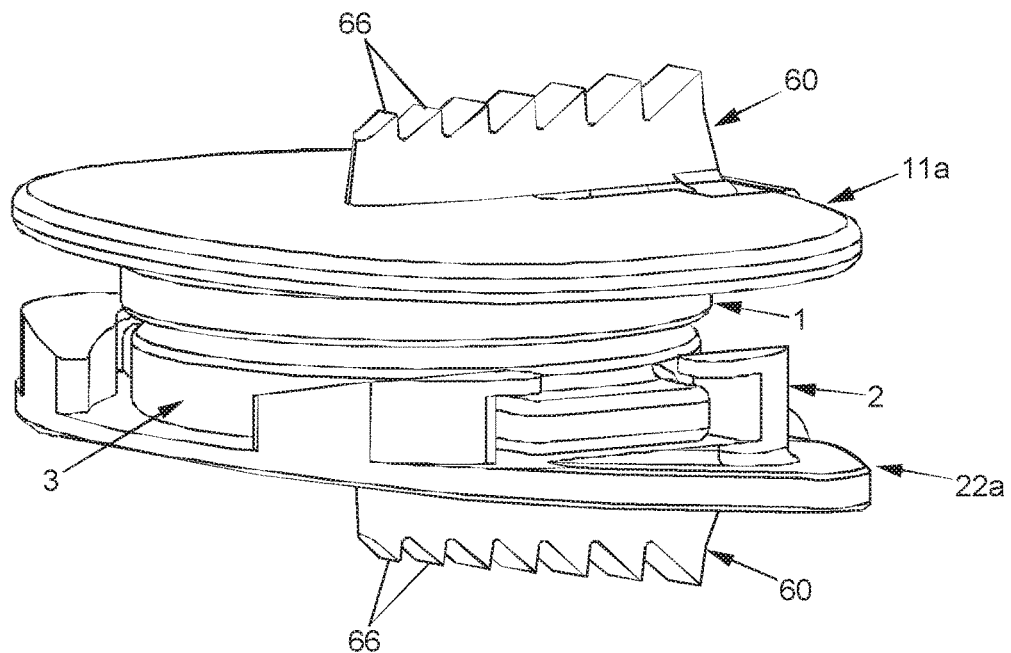
FIGS. 10A and 10B illustrate perspective views of, respectively, the prosthesis comprising osseous anchorage means according to an embodiment of the present invention and one of the osseous anchorage means according this embodiment.
Figure 10B:
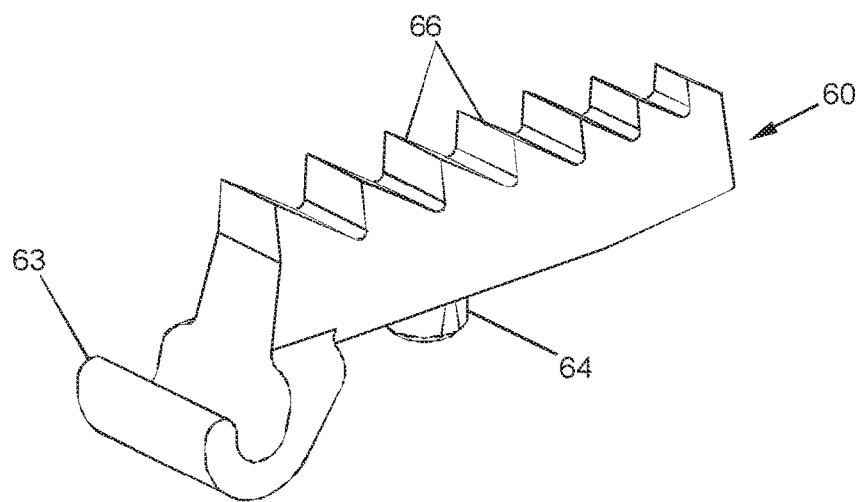
Figure 11A:
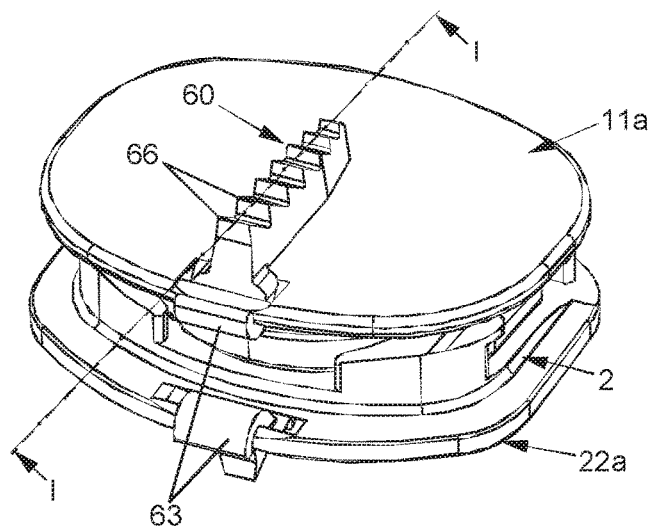
FIGS. 11A and 11B respectively illustrate a perspective view of the prosthesis comprising osseous anchorage means according to an embodiment of the present invention and a cross section view along plane I-I of FIG. 11A.
Figure 11B:
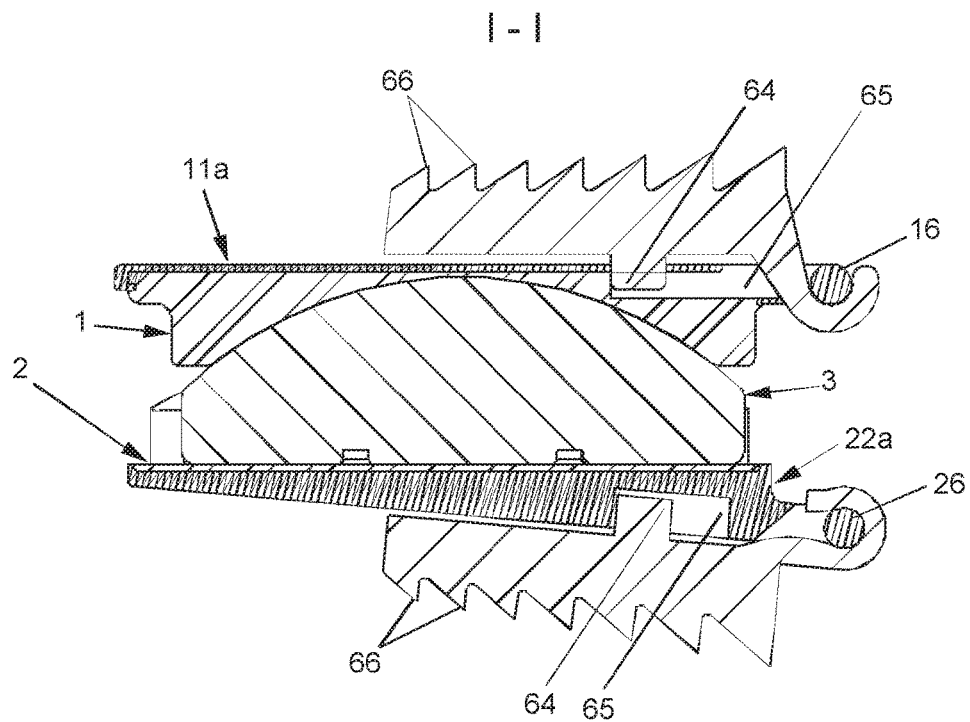

Those of ordinary skill will recognize that the present prosthesis can comprise other osseous anchorage means (60) than those described above, without departing from the scope of the present invention. To give non-limitative examples, such osseous anchorage means (60) can consist of winglets fixed on the prosthesis as in the Patent Application WO03/039400 or of a stud nailed in the vertebra through the anatomic adaptation elements as in the Patent Application WO04/041129. One embodiment of the anchorage means (60) is presented on the FIGS. 10A, 10B, 11A and 11B. Osseous anchorage means (60) according to this embodiment consist of winglets comprising a hooked part (63), curved to fold over itself, so that the winglets can be adapted onto the anatomic adaptation elements. Hooked part (63) of the winglet, particularly visible on FIG. 10B, allows the anchorage means (60) to be interlocked onto the edge (16, 26) of an opening made in the vicinity of the periphery of the anatomic adaptation plates (11a, 22a), as particularly visible on FIGS. 11A and 11B. This edge (16, 26) of the opening creates a sort of rod onto which the osseous anchorage means (60) interlock, as described above. The winglet further comprises a pin (64) (or a dowel) adapted to be inserted into a groove (65) present on the surface of the plate and/or the anatomic adaptation element on which the winglet is to be fixed, as particularly visible on FIG. 11B. The groove (65) and the pin (64) have dimensions adapted so that the pin (64) is secured into groove (65). For example, pin (64) may have a substantially conical shape, with the larger diameter of the cone being at the base of the pin and the smaller diameter being at its end. Groove (65) may have side walls adapted to cooperate with the conical shape of the pin (64) so that the pin tightly fits inside the groove and thus secures the osseous anchoring means (60) onto anatomic adaptation plates (11a, 22a). For example, the width of the groove (65) may be larger at its surface than at its bottom. The osseous anchorage means (60) are thus fixed onto the prosthesis by first interlocking hooked part (63) onto rod-like edge (16, 26) of anatomic adaptation plates (11a, 22a) and by rotating osseous anchorage means (60) the rod until pin (64) penetrates into groove (65) of anatomic adaptation plate (11a, 22a) and/or of plate (1, 2). Winglet (60) may have a standard size for many of the embodiments and the position of pin (64) of winglet (60) inside groove (65) may vary as a function of the size of anatomic adaptation plates (11a, 22a). Depending on the thickness of anatomic adaptation plates (11a, 22a), pin (64) penetrates into anatomic adaptation plates (11a, 22a) or may traverse anatomic adaptation plates (11a, 22a) and penetrate into a groove (65) in plates (1, 2), as shown for example on FIG. 11B for upper plate (1). Since the anatomic adaptation plates (11a, 22a) may vary in size (diameter), their groove may have variable lengths and can be replaced by a hole having a variable distance from the rod-like edge (16, 26) so that the hole is adapted to receive the pin (64). When the pin is designed to penetrate the plates also, the plates will typically include a groove because the distance of the pin from the periphery of the plates will vary depending on the size of the anatomic adaptation plates (11a, 22a). Once secured onto the anatomic adaptation plates (11a, 22a), winglets (60) are adapted to cooperate with a groove drilled in the surfaces of the adjacent vertebrae with which they are in contact. Thus, the surgeon may create a groove in the surfaces of vertebrae between which the prosthesis is intended to be inserted. This groove in the vertebrae may have an orientation relative to the sagittal plane that will depend on the position and orientation of the winglet. This orientation may be predetermined and may then set and secure the orientation of the prosthesis. Similarly, the depth of the groove in the vertebrae and its extend from the periphery will be predetermined as a function of the size of winglet (60) and may allow the surgeon to adjust the relative position of the various elements of the prosthesis and predict the position of the prosthesis relative to the natural axis of the vertebrae. The winglets typically comprise notches (66) on their surfaces which are intended to be in contact with the bottom of the groove preformed in the vertebrae. Notches (66) of winglets (60) will resist against the ejection of the prosthesis from inside its housing between the vertebrae, such as for example when strong constraints are applied to the prosthesis. With reference to FIG. 11B, hooked part (63) of the winglets (60) can be oriented so that they are to be interlocked onto the rod-like edge (16, 26) by being inserted inside the opening made in the vicinity of the periphery of the anatomic adaptation plates (11a, 22a) or by being inserted from outside this opening.

The osseous anchoring means (60) described above are adapted to anatomic adaptation plates (11a, 22a) but may also be adapted to anatomic adaptation crowns (11b, 22b) comprising an opening in the vicinity of their periphery or to the plates of other types of intervertebral disc prosthesis having plates comprising an opening in the vicinity of their periphery. The edge (16, 26) of such opening in the plates create a sort of rod onto which the hooked part (63) of both removable embodiments of the osseous anchoring means (60) can be interlocked.

FIGS. 4 to 9 illustrate plates (1, 2) of the prosthesis traverse equipped with anatomic adaptation elements (11, 22) and illustrate different exemplar embodiments of fixation means (113, 223, 15, 25) of these anatomic adaptation elements (11, 22) on plates (1, 2). Fixation means (113, 223, 15, 25) are in some embodiments, reversible, this means that anatomic adaptation elements (11, 22) can be attached and removed from plates (1, 2) of the prosthesis. Fixation means (113, 223, 15, 25) thus allow anatomic adaptation elements (11, 22), fixable in a moveable manner to plates (1, 2), to be changed. Fixation means (113, 223, 15, 25) of anatomic adaptation elements (11, 22) on plates (1, 2) consist of fixation means (113, 223) present on anatomic adaptation elements (11, 22) and complementary with fixation means (15, 25) present on the plates (1, 2) of the prosthesis. Anatomic adaptation elements (11, 22) are fixed onto plates (1, 2) via, contact of at least a part of their lower (111) face (which, for example, may be lower surfaces 111a or lower edges 111b) and upper (222) face (which, for example, may be upper surfaces 222a or upper edges 222b) with at least a part upper (1) and lower (2) plates and, on the other hand, contact of their fixation means (113, 223) with complementary fixation means (15, 25) present on plates (1, 2) of the prosthesis. For anatomic plates (11a, 22a) such as those illustrated, for example, in FIGS. 4A to 4D, anatomic adaptation elements (11, 22) are fixed onto plates (1, 2) with upper (10) and lower (20) surfaces of upper (1) and lower (2) plates which are attached to reinforcements present on lower (111a) and upper (222a) surfaces respectively of the upper (11) and lower (22) anatomic plates, via fixation means (113, 223, 15, 25). For anatomic crowns (11b, 22b) such as those illustrated, for example, in FIGS. 5A to 5C, anatomic adaptation elements (11, 22) are fixed onto plates (1, 2) with bevelled parts of upper (10) and lower (20) surfaces, respectively of upper (1) and lower (2) plates which are attached to bevelled parts of upper (111b) and lower (222b) edges of upper (11) and lower (22) anatomic crowns, via fixation means (113, 223, 15, 25). Different embodiments of fixation means (113, 223, 15, 25) of anatomic adaptation elements (11, 22) on plates (1, 2) will now be described in reference to FIGS. 4 to 9. These fixation means are given by way of illustration and can be replaced by other means such as will be recognized by those of skill. A variety of combinations of the different fixation means (113, 223, 15, 25) are described below.

In several embodiments, fixation means (113, 223, 15, 25) of anatomic adaptation elements (11, 22) on plates (1, 2) consist of male fixation means (113, 223) present on anatomic adaptation elements (11, 22) and cooperate with female fixation means (15, 25) present on plates (1, 2) of the prosthesis. Female fixation means (15, 25) present on plates (1, 2) of prosthesis can consist, for example, in plane surfaces (15, 25) present on edges of plates (1, 2) of the prosthesis or in recesses (15, 25) either made in the edges of the plates (1, 2) of the prosthesis, or in the edges of female cooperation means (23) of plates (1, 2) of the prosthesis.

Figure 4A:
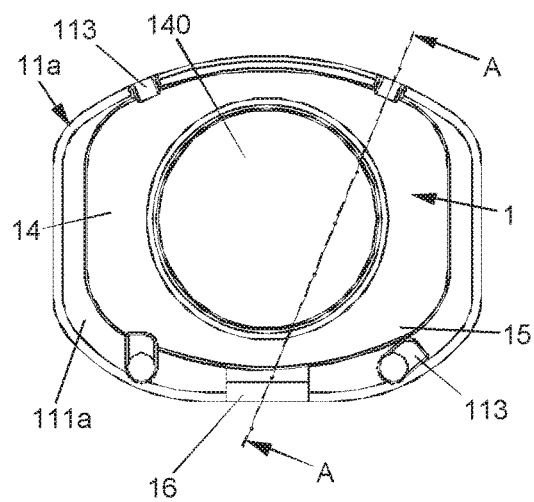
FIGS. 4A and 4B respectively illustrate a bottom view and a cross section view along plane A-A in FIG. 4A, of the upper plate equipped with its anatomic adaptation element, according to an embodiment of the invention, FIGS. 4C and 4D respectively illustrate a plan view and a cross section view along plane B-B in FIG. 4C, of the upper plate equipped with its anatomic adaptation element, according to an embodiment of the invention.
Figure 4B:
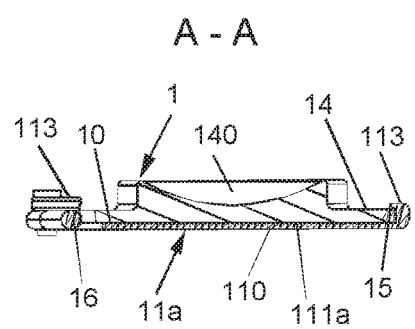
Figure 4C:
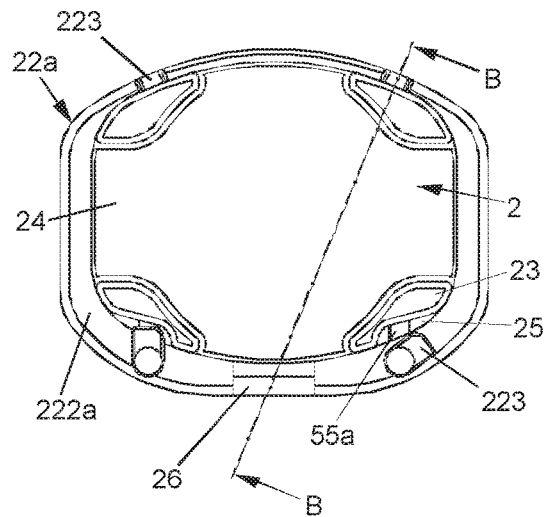
Figure 4D:
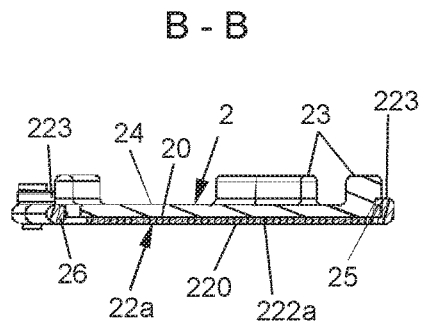

In an embodiment illustrated in FIGS. 4A and 4B, fixation means (113) of upper anatomic plate (11a) consist, on posterior edge of lower surface (111a), in nibs which are shaped and have dimensions intended to receive a section (15) of posterior edge of lower surface (14) of upper plate (1). On an anterior edge of its lower surface (111a), fixation means (113) of upper anatomic plate (11a) consists in latches constituted in an axis of rotation onto which a hasp is mounted to swivel about this axis and receive a section (15) of posterior edge of lower surface (14) of upper plate (1), as shown in FIGS. 4A and 4B. Right-hand latches in FIGS. 4A to 4C are illustrated in the open position and the left-hand latches are in the closed position. In the embodiment illustrated in FIGS. 4C and 4D, fixation means (223) of lower anatomic plate (22a) consist, on the posterior edge of lower surface (222a), in nibs which are shaped and have dimensions to fit into opening (25) made in cooperation means (23) of lower plate (2). On anterior edge of its lower surface (222a), fixation means (223) of upper anatomic plate (22a) consist of latches constituted in an axis of rotation onto which a hasp is mounted intended to receive a recess (25) made in a part of cooperation means (23) present on posterior edge of the lower plate (2). Latches illustrated in FIGS. 4A to 4D can be maintained in the closed position via securing means (55) present, for example, on plates (1, 2) of the prosthesis. For example, as illustrated in FIG. 4C, a notch (55a) made on recess (25) present on a part of the cooperation means (23) of the lower plate (2) prevents latch (223) of lower anatomic plate (22a) from swiveling.

Figure 5A:
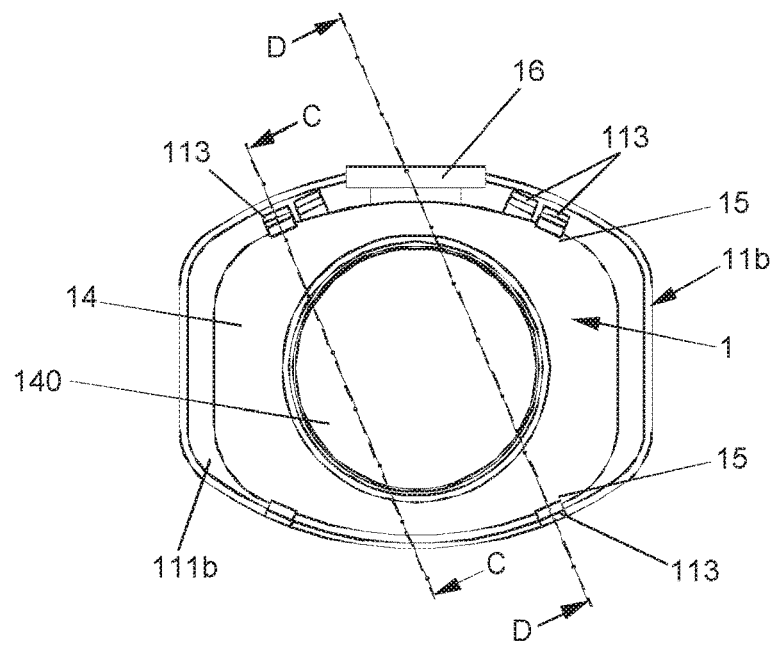
FIG. 5A illustrates a bottom view of the upper plate equipped with its anatomic adaptation element, according to an embodiment of the invention.
Figure 5B:
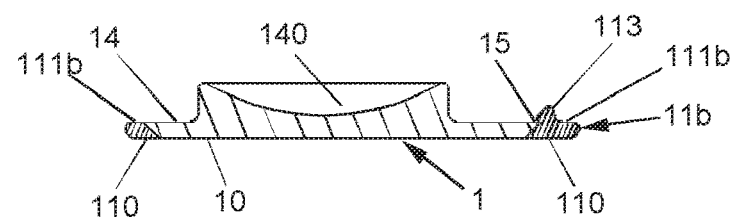
FIGS. 5B and 5C illustrate cross section views respectively along plane C-C and plane D-D in FIG. 5A, of the upper plate equipped with its anatomic adaptation element, according to this embodiment of the invention.
Figure 5C:
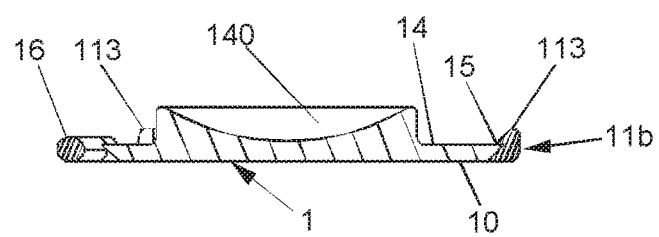

In the embodiment in FIGS. 5A to 5C, anterior and posterior edges of the upper anatomic adaptation crowns (11b) have fixation means (113) consisting in nibs which cooperate with a plane section (15) present on the edge of the lower surface (14) of the upper plate.

In the embodiments in FIGS. 6A to 9D, fixation means (113, 223, 15, 25) of anatomic adaptation elements (11, 22) on plates (1, 2) consist in female fixation means (113, 223) present on anatomic adaptation elements (11, 22) and cooperating with male intermediary means (50) which can also cooperate with female fixation means (15, 25) present on plates (1, 2) of the prosthesis. Anatomic adaptation elements (11, 22) are fixed onto plates (1, 2) via, contact of at least a part of their upper (111) and lower (222) faces with at least a part, respectively of the upper (1) and lower (2) plates and, on the other hand, contact of male intermediary means (50) with female fixation means (113, 223) present on anatomic adaptation elements (11, 22) and with female fixation means (15, 25) present on plates (1, 2) of the prosthesis. Male intermediary means (50) consist in a sliding plate (50) in female fixation means (113, 223) present on anatomic adaptation elements (11, 22) to cooperate with female fixation means (15, 25) present on plates (1, 2) of prosthesis. Plate (50) is substantially parallelepiped in shape and can comprise, on its side edges, fins (500), particularly visible, for example, in FIG. 7A. Fins (500) of the male intermediary means (50) are of complementary shape with female fixation means (113, 223) of anatomic adaptation elements (11, 22) and with female fixation means (15, 25) of plates (1, 2) of prosthesis, which have side runners in which these fins (500) slide. This complementary shape of the fins (500) of the plate (50) and the runners of the female fixation means (113, 223) of anatomic adaptation elements (11, 22) as well as the female fixation means (15, 25) of plates (1, 2) prevent plate (50) from leaving these female fixation means (113, 223, 15, 25) prior to being secured via the securing means (55).

Male intermediary means (50) have securing means (55) blocking the male intermediary means (50) in the position where they cooperate with both the female fixation means (113, 223) of the anatomic adaptation elements (11, 22) and with the female fixation means (15, 25) present on the plates (1, 2) of the prosthesis. Securing means (55) which consist, for example, in at least an irregularity (for example, notches 55a, slots 55b, or other variants) present on at least one side of plate (50) and to cooperate with at least an opening (550) made in female fixation means (113, 223) of anatomic adaptation elements (11, 22) and/or in female fixation means (15, 25) of plates (1, 2). Opening (550) can be of a complementary shape of male intermediary means (50) or of its securing means, as illustrated in FIGS. 6A and 6B.

Figure 6A:
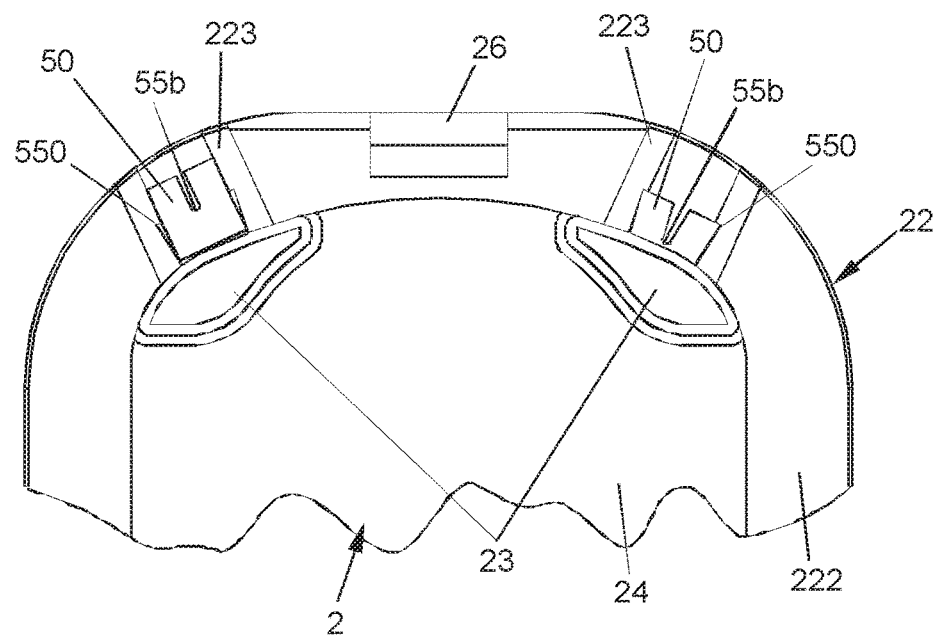
FIGS. 6A and 6B illustrate bottom views of a part of the upper plate equipped with its anatomic adaptation element, according to two different embodiments of the invention.
Figure 6B:
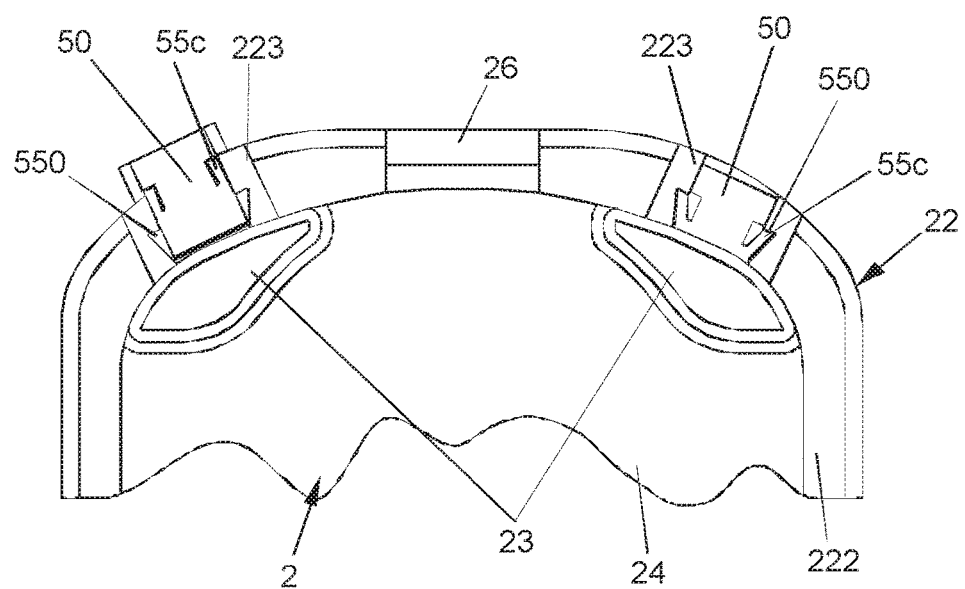
Figure 7A:
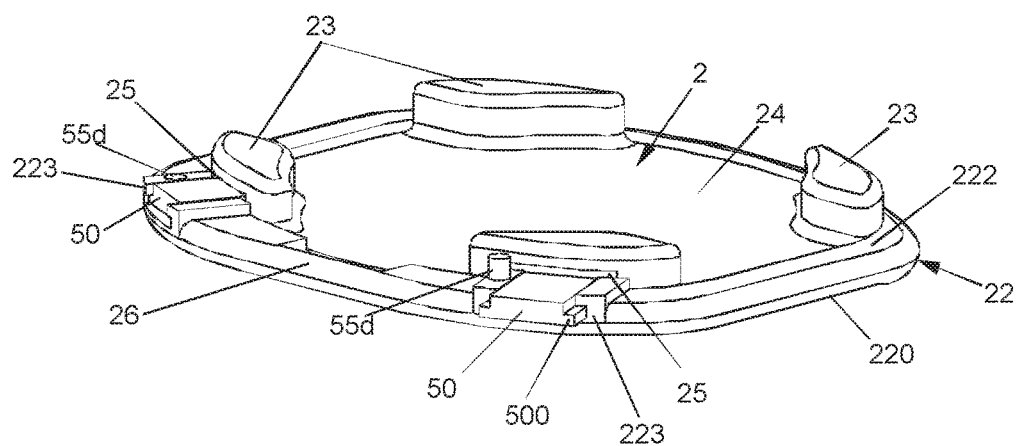
FIGS. 7A and 7B illustrate perspective views of the lower plate equipped with its anatomic adaptation element, according to two different embodiments of the invention.
Figure 7B:
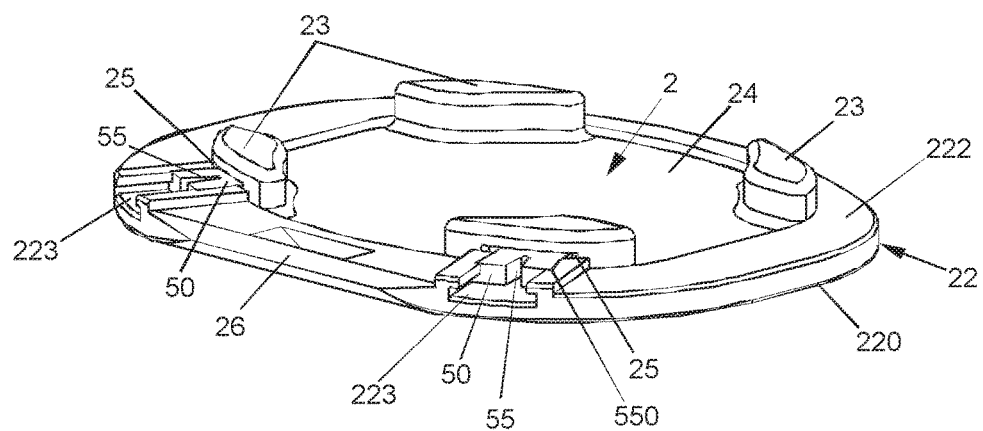

In the embodiment illustrated in FIG. 6A, the plate constituting male intermediary means (50) widens out towards its posterior end and the irregularity constituting the exemplar securing means (55) comprises a slot (55b) on the posterior half of the plate (50). This slot (55b) compresses the posterior end of the plate (50) when it is introduced into the female fixation means (113, 223) of the upper and/or lower anatomic adaptation elements (11, 22), as illustrated for the left-hand plate in FIG. 6A. When plate (50) reaches its end of stroke in the runner created by the female means (113, 223) of anatomic adaptation elements (11, 22) and means (15, 25) of plates (1, 2), meaning when it cooperates with these two female means at the same time, openings (550) made, for example, in the female means (113, 223) of the anatomic adaptation elements (11, 22) separate the plate (50) from its hold. This is illustrated for the right-hand plate in FIG. 6A. FIG. 7B illustrates a perspective view of this embodiment of fixation means in which plate (50) is intended to be held in female manes (25) made in cooperation means (23) of lower plate (2). This figure also shows the reinforcement present, for example, on lower anatomic plate (22a) may be deeper than the thickness of the lower plate (2). Depending on the size of cooperation means (23, 33) of lower plate (2) of core (3), the edges of this reinforcement may provide a periphery abutment possibly limiting the displacement of core (3) in relation to lower plate (2). In the embodiment illustrated in FIG. 6B, irregularities constituting securing means (55) of male intermediary means (50) consist in hasps present on the side edges of the plate (50). As illustrated for left-hand plate (50) in FIG. 6B, these hasps (55c) are compressed when hasp is introduced into the runners of female means (113, 223). When the plate is pushed as far as the blocking position, hasps (55c) open out in openings (550) provided for on the side edges of the female means (113, 223) of upper and/or lower anatomic adaptation elements (11, 22), as illustrated for right-hand plate (50) in FIG. 6B.

Figure 8A:
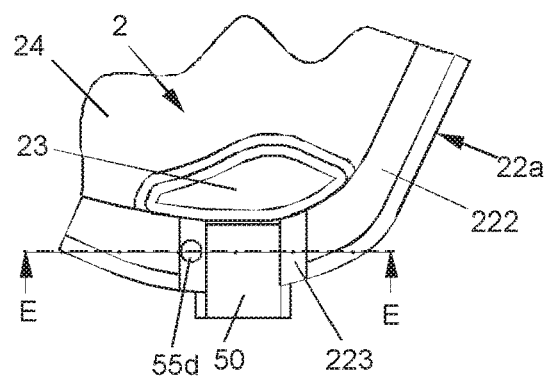
FIGS. 8A and 8B respectively illustrate a bottom view and a cross section view along plane E-E in FIG. 8A, of a part of the lower plate equipped with its anatomic adaptation element whose fixation means are open, according to an embodiment of the invention, FIGS. 8C and 8D respectively illustrate a bottom view and a cross section view along plane F-F in FIG. 8C, of the same embodiment as in FIGS. 8A and 8B, but with the fixation means of the anatomic adaptation element closed and locked, according to an embodiment of the invention.
Figure 8A:
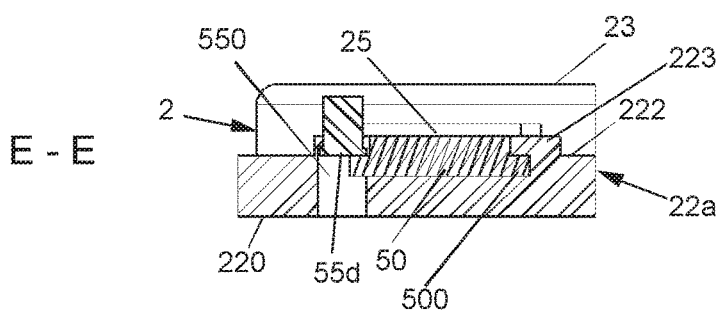
Figure 8C:
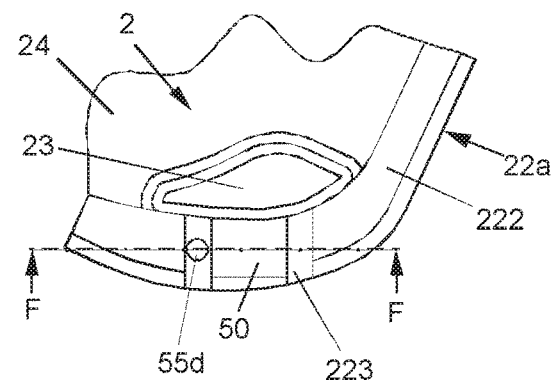
Figure 8C:
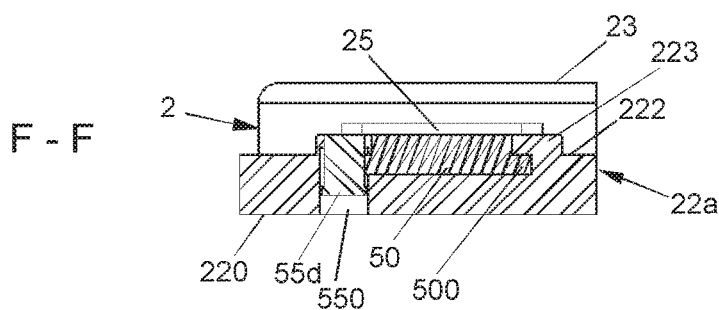

FIGS. 7A and 8A to 8D illustrate another alternative embodiment of the male intermediary means (50). In this embodiment, irregularities of plate (50) constituting the securing means (55) of plate (50) consist in a bore in male intermediary means (50), prolonged by a bore (550) in a female fixation means (113, 223) of anatomic adaptation elements (11, 22), as particularly visible in FIG. 8B. The bore (550) is intended to receive a securing pin (55d) blocking the male intermediary means (50) in the position where they cooperate with female fixation means (15, 25) present on the plates (1, 2) of prosthesis, as illustrated in FIG. 8C.

Figure 9A:
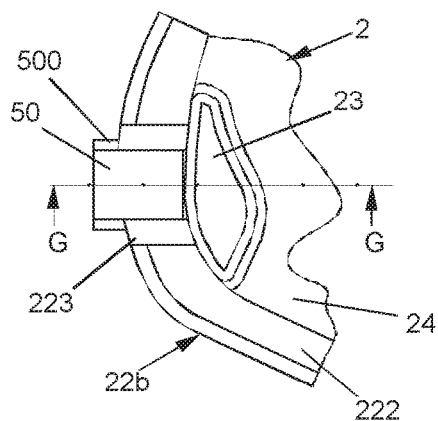
FIGS. 9A and 9B respectively illustrate a bottom view and a cross section view along plane G-G in FIG. 9A, of a part of the lower plate equipped with its anatomic adaptation element whose fixation means are open, according to an embodiment of the invention, FIGS. 9C and 9D respectively illustrate a bottom view and a cross section view along plane H-H in FIG. 9C, of the same embodiment as in FIGS. 9A and 9B, but with the fixation means of the anatomic adaptation element closed and locked, according to an embodiment of the invention.
Figure 9B:
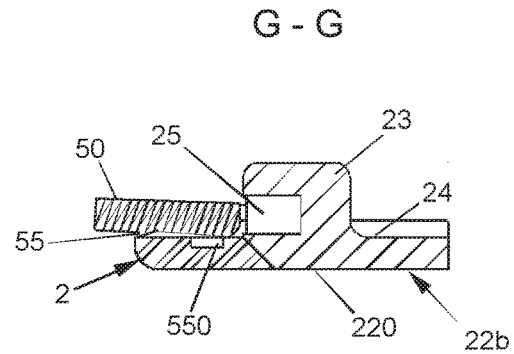
Figure 9C:
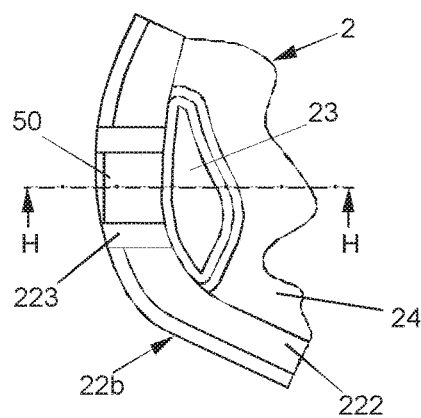
Figure 9D:
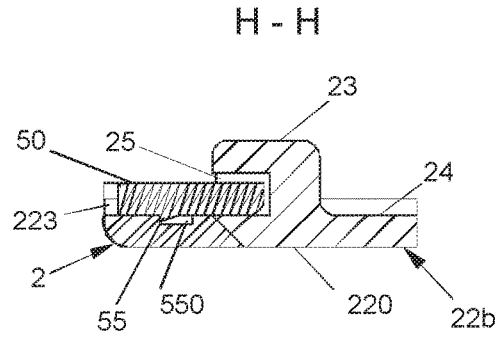

Another alternative of the securing means (55) of male intermediary means (50) is illustrated in FIGS. 9A to 9D. In this alternative, the irregularities constituting securing means (55) of plate (50) consist of a notch (55a) present on the lower surface of the plate and cooperative with an opening (550) made in the female fixation means (113, 223) of anatomic adaptation elements by resisting against removal of plate (50), once driven as far as the female fixation means (15, 25) of the plates (1, 2), as illustrated in FIG. 9D.

It will be evident to those of ordinary skill that the invention allows embodiments in numerous other specific forms without departing from the scope of the invention. The embodiments are offered, therefore, only to illustrate rather than limit the invention which is limited only by the following claims:

The invention claimed is:

1. An intervertebral disc prosthesis comprising:
an elongated movable osseous anchor comprising an insertion end disposed at a first longitudinal end of the anchor and a retention end disposed at a second longitudinal end of the anchor, a plate-like body disposed between the insertion end and the retention end, and a curved portion disposed proximal to the retention end;
an upper prosthesis plate;
a lower prosthesis plate comprising a first stop disposed along a first edge of the lower prosthesis plate, a second stop disposed along a second edge of the lower prosthesis plate opposite to the first edge of the lower prosthesis plate, a rear edge disposed between the first stop and the second stop, and a passage through the lower prosthesis plate disposed along the rear edge of the lower prosthesis plate and sized to accept the plate-like body and configured to position the curved portion at least partially around the edge with the insertion end extending away from the lower prosthesis plate; and
a core translatable with respect to the lower prosthesis plate and comprising a third stop and a fourth stop, the third stop configured to cooperatively abut the first stop and the fourth stop configured to cooperatively abut the second stop to limit translation of the core with respect to the lower prosthesis plate.

2. The device of claim 1 in which the curved portion folds over and projects a plate-like extension disposed adjacent the plate-like body.

3. The device of claim 2 in which the plate-like extension comprises an end disposed distal to the retention end and proximal to the insertion end.

4. The device of claim 2 in which the plate-like extension comprises an end disposed distal to the retention end and proximal to the curved portion.

5. The device of claim 2 in which the plate-like body and the plate-like extension each comprises retention notches on opposite edges.

6. The device of claim 1 in which the curved portion interlocks on the rear edge of the lower prosthesis plate.

7. The device of claim 6 in which the passage is configured to permit a variable angle of interlock.

8. A device for insertion between adjacent vertebrae of a spine, the device comprising:
a vertebral contact surface;
a retainer disposed along the edge of the vertebral contact surface;
a fixation recess disposed on the vertebral contact surface; and
an elongated winglet-shaped anchor comprising a first longitudinal end and an opposite second longitudinal end, a side configured for placement adjacent the vertebral contact surface, a curved retainer disposed at the first longitudinal end and configured to at least partially encircle the retainer, and a projection extending from the side configured to engage the fixation recess with the anchor placed adjacent the vertebral contact surface with the curved retainer at least partially encircling the retainer.

9. The device of claim 8 in which the curved retainer disposed at the first longitudinal end of the anchor is configured to interlock with the retainer on the vertebral contact surface.

10. The device of claim 8 in which the fixation recess is a groove.

11. The device of claim 8 in which the projection is a pin or a dowel.

12. The device of claim 11 in which the projection is conically shaped.

13. The device of claim 8 in which the fixation recess comprises walls configured complementary to the sides of the projection.

14. The device of claim 8 further comprising notches along a side of the anchor opposite the side of the anchor configured for placement adjacent the vertebral contact surface.

15. An intervertebral disc prosthesis comprising:
an upper prosthesis plate comprising a passage disposed proximally to a first edge of the upper prosthesis plate, a lower prosthesis plate having a peripheral edge, and a core having a peripheral edge, the upper prosthesis plate, the lower prosthesis plate, and the core being configured for movement of the core at least in translation at least in relation to the lower prosthesis plate along an axis substantially parallel to the lower prosthesis plate when the prosthesis is assembled;

a stop disposed along the peripheral edge of the core and a stop disposed proximal to the peripheral edge of the lower prosthesis plate, with the stops sized and configured with portions that cooperatively abut to limit the range of movement in translation of the core relative to the lower prosthesis plate along an axis substantially parallel to the lower prosthesis plate and to limit the rotation of the core relative to the lower prosthesis plate about an axis substantially perpendicular to the lower prosthesis plate; and an elongated movable osseous anchor comprising an insertion end disposed at a first longitudinal end of the anchor, a retention end disposed at a second longitudinal end of the anchor, a plate-like body disposed between the insertion end and the retention end, and a curved portion disposed proximal to the retention end.

16. The device of claim 15 in which the curved portion folds over and projects a plate-like extension disposed adjacent the plate-like body.

17. The intervertebral disc prosthesis of claim 16 in which the plate-like extension comprises an end disposed distal to the retention end and proximal to the insertion end.

18. The intervertebral disc prosthesis of claim 16 in which the plate-like extension comprises an end disposed distal to the insertion end and proximal to the curved portion.

19. The intervertebral disc prosthesis of claim 16 in which the plate-like body and the plate-like extension each comprises retention notches on opposite edges.

20. The intervertebral disc prosthesis of claim 15 in which the curved portion interlocks on the edge of the upper vertebral contact surface.

* * * * *